(12) United States Patent
Gallion et al.

(10) Patent No.: US 6,693,072 B2
(45) Date of Patent: Feb. 17, 2004

(54) ELASTASE INHIBITORS

(75) Inventors: Steven L. Gallion, Woburn, MA (US); William A. Metz Jr., Loveland, OH (US); Joseph P. Burkhart, Plainfield, IN (US); Michael R. Angelastro, Mason, OH (US); Norton P. Peet, Cincinnati, OH (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 174 days.

(21) Appl. No.: 09/741,536

(22) Filed: Dec. 20, 2000

(65) Prior Publication Data

US 2003/0096759 A1 May 22, 2003

Related U.S. Application Data

(63) Continuation of application No. 08/737,235, filed as application No. PCT/US95/05618 on May 5, 1995, now abandoned, which is a continuation-in-part of application No. 08/252,799, filed on Jun. 2, 1994, now abandoned.

(51) Int. Cl.$^7$ ............................................... A61K 38/00
(52) U.S. Cl. ............................... 514/2; 514/18; 514/19; 530/330; 530/331
(58) Field of Search ............... 514/2, 18, 19, 514/17, 183; 530/323, 330, 331, 328

(56) References Cited

U.S. PATENT DOCUMENTS 4,783,523 A * 11/1988 Urry .......................... 530/323
4,898,926 A * 2/1990 Urry .......................... 528/328
4,910,190 A * 3/1990 Bergeson et al. ............. 514/19
4,935,493 A * 6/1990 Bachovchin et al. ........ 530/331

FOREIGN PATENT DOCUMENTS

EP        0189305     *  7/1986  ............ C07K/5/06

OTHER PUBLICATIONS

Imperiali et al. Inhibition of serine proteases by peptidyl fluoromethyl ketones. Biochem. (1986) 25: 3760–3767.*
Ueda et al. The synthesis of arginylfluoroalkanes, their inhibition of trypsin and blood–coagulation serine proteinases and their anticoagulant activity. Biochem. J. (1990) 265: 539–45.*
Angelastro et al. Inhibition of human neutrophil elastase with peptidyl electrophilic ketones. 2. Orally active pg–val––pro–val pentafluoroethyl ketones. Journal of Medicinal Chem. (1994) 37(26): 4538–53.*
Burkhart et al. Inhibition of human neutrophil elastase. 3. An orally active enol acetate prodrug. Journal of Medicinal Chem. (1995) 38(2): 223–33.*

* cited by examiner

*Primary Examiner*—Brenda Brumback
*Assistant Examiner*—Maury Audet
(74) *Attorney, Agent, or Firm*—Joseph Strupczewski

(57) ABSTRACT

This invention relates to compounds which are inhibitors of elastase, particularly human neutrophil elastase. The inhibitors are short, synthetic peptides in which the $P_2$ moiety is substituted with various nitrogen-containing heterocyclic groups. As inhibitors of human neutrophil elastase, the compounds are useful in the treatment of a patient afflicted with a neutrophil associated inflammatory disease.

11 Claims, No Drawings

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Chemically synthesized peptide with sequence selected to inhibit human neutrophil elastase.
<220> FEATURE:
<221> NAME/KEY: MISC_FEATURE
<222> LOCATION: (1)..(1)
<223> OTHER INFORMATION: Ala, bAla, Leu, Ile, Val, Nva, bVal, Nle
<220> FEATURE:
<221> NAME/KEY: MISC_FEATURE
<222> LOCATION: (2)..(2)
<223> OTHER INFORMATION: Ala, bAla, Leu, Ile, Val, Nva, bVal, Nle, Pro, Ind, Tic, Tca, Lys
<220> FEATURE:
<221> NAME/KEY: MISC_FEATURE
<222> LOCATION: (3)..(3)
<223> OTHER INFORMATION: Pip, Aze, Pro
<220> FEATURE:
<221> NAME/KEY: MISC_FEATURE
<222> LOCATION: (4)..(4)
<223> OTHER INFORMATION: Ala, Leu, Ile, Val, Nva, bVal

```
<400> SEQUENCE: 1

Xaa Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: Chemically synthesized peptide with sequence
      selected to inhibit human neutrophil elastase.
<220> FEATURE:
<221> NAME/KEY: MISC_FEATURE
<222> LOCATION: (1)..(1)
<223> OTHER INFORMATION: Ala, bAla, Leu, Ile, Val, Nva, bVal, Nle
<220> FEATURE:
<221> NAME/KEY: MISC_FEATURE
<222> LOCATION: (2)..(2)
<223> OTHER INFORMATION: Ala, bAla, Leu, Ile, Val, Nva, bVal, Nle, Pro,
      Ind, Tic, Tca, Lys
<220> FEATURE:
<221> NAME/KEY: MISC_FEATURE
<222> LOCATION: (3)..(3)
<223> OTHER INFORMATION: Pip, Aze, Pro
<220> FEATURE:
<221> NAME/KEY: MISC_FEATURE
<222> LOCATION: (4)..(4)
<223> OTHER INFORMATION: Ala, Leu, Ile, Val, Nva, bVal

<400> SEQUENCE: 2

Xaa Xaa Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: Chemically synthesized peptide with sequence
      selected to inhibit human neutrophil elastase.
<220> FEATURE:
<221> NAME/KEY: MISC_FEATURE
<222> LOCATION: (1)..(1)
<223> OTHER INFORMATION: Ala, bAla, Leu, Ile, Val, Nva, bVal, Nle
<220> FEATURE:
<221> NAME/KEY: MISC_FEATURE
<222> LOCATION: (2)..(2)
<223> OTHER INFORMATION: Ala, bAla, Leu, Ile, Val, Nva, bVal, Nle, Pro,
      Ind, Tic, Tca, Lys
<220> FEATURE:
<221> NAME/KEY: MISC_FEATURE
<222> LOCATION: (3)..(3)
<223> OTHER INFORMATION: Pip, Aze, Pro
<220> FEATURE:
<221> NAME/KEY: MISC_FEATURE
<222> LOCATION: (4)..(4)
<223> OTHER INFORMATION: Ala, Leu, Ile, Val, Nva, bVal

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Chemically synthesized peptide with sequence
      selected to inhibit human neutrophil elastase.
<220> FEATURE:
<221> NAME/KEY: MISC_FEATURE
<222> LOCATION: (1)..(1)
```

```
<223> OTHER INFORMATION: Ala, bAla, Leu, Ile, Val, Nva, bVal, Nle
<220> FEATURE:
<221> NAME/KEY: MISC_FEATURE
<222> LOCATION: (2)..(2)
<223> OTHER INFORMATION: Ala, bAla, Leu, Ile, Val, Nva, bVal, Nle, Pro,
      Ind, Tic, Tca, Lys
<220> FEATURE:
<221> NAME/KEY: MISC_FEATURE
<222> LOCATION: (3)..(3)
<223> OTHER INFORMATION: Pip, Aze, Pro
<220> FEATURE:
<221> NAME/KEY: MISC_FEATURE
<222> LOCATION: (4)..(4)
<223> OTHER INFORMATION: Ala, Leu, Ile, Val, Nva, bVal

<400> SEQUENCE: 4

Xaa Xaa Xaa Xaa
1
```

ELASTASE INHIBITORS

This application is a continuation of application Ser. No. 08/737,235, filed Nov. 20, 1996, now abandoned, which is a national stage entry under 35 U.S.C. §371 of an International Application No. PCT/US95/05618, filed May 5, 1995, which is a continuation-in-part of application Ser. No. 08/252,799, filed Jun. 2, 1994, now abandoned.

BACKGROUND OF THE INVENTION

This invention relates to compounds which are inhibitors of elastase, particularly human neutrophil elastase, useful for a variety of physiological and end-use applications. Human neutrophil elastase has been implicated as an agent contributing to the tissue destruction associated with a number of inflammatory diseases such as chronic bronchitis, cystic fibrosis, and rheumatoid arthritis. J. L. Malech and J. I. Gallin, *New Engl. J. Med.*, 317(11), 687 (1987). Elastase possesses a broad range of proteolytic activity against a number of connective tissue macromolecules including elastin, fibronectin, collagen, and proteoglycan. The presence of the enzyme elastase may contribute to the pathology of these diseases.

Normal plasma contains large quantities of protease inhibitors that control a variety of enzymes involved in connective tissue turnover and inflammation. For example, α-1-proteinase inhibitor α-1-PI) is a serine protease inhibitor that blocks the activity of elastase. α-1-PI has received considerable interest because reduction in plasma levels to less than 15% of normal is associated with the early development of emphysema. In addition to plasma derived protease inhibitors, secretory fluids, including bronchial, nasal, cervical mucus, and seminal fluid contain an endogenous protease inhibitor called secretory leukoprotease inhibitor (SLPI) that can inactivate elastase and is believed to play an important role in maintaining the integrity of the epithelium in the presence of inflammatory cell proteases. In certain pathological states α-1-PI and SLPI are inactivated by neutrophil oxidative mechanisms allowing the neutrophil proteases to function in an essentially inhibitor-free environment. For example, bronchial lavage fluids from patients with adult respiratory distress syndrome (ARDS) have been found to contain active elastase and α-1-PI that had been inactivated by oxidation.

In addition to oxidative mechanisms, neutrophils possess non-oxidative mechanisms for eluding inhibition by antiproteases. Neutrophils from patients with chronic granulomatous disease are capable of degrading endothelial cell matrices in the presence of excess α-1-PI. There is considerable in vitro evidence that stimulated neutrophils can tightly bind to their substrates such that serum antiproteases are effectively excluded from the microenvironment of tight cell-substrate contact. The influx of large numbers of neutrophils to an inflammatory site may result in considerable tissue damage due to the proteolysis that occurs in this region.

Applicants have determined that elastase is one of the primary neutrophil proteases responsible for cartilage matrix degeneration as measured by the ability of neutrophil lysate, purified elastase and stimulated neutrophils to degrade cartilage matrix proteoglycan. Furthermore, applicants have previously discovered peptide derivatives useful as elastase inhibitors, exerting valuable pharmacological activities. For example, peptide derivatives useful as elastase inhibitors wherein the terminal carboxyl group has been replaced by a pentafluoroethylcarbonyl (—C(O)C$_2$F$_5$)group and in which the N-terminal amino acid is protected by various heterocycle-containing groups such as a 4-morpholinecarbonyl group are disclosed in European Patent Application OPI No. 0529568, inventors Peet et al., with a publication date of Mar. 3, 1993. Applicants have recently discovered peptidyl elastase inhibitors in which the P$_2$ moiety is substituted with various nitrogen-containing heterocyclic groups.

SUMMARY OF THE INVENTION

The present invention relates to compounds having the following formula I

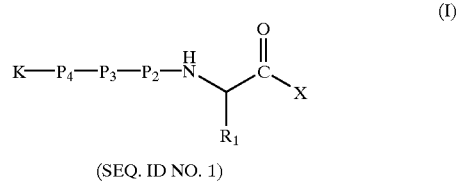

(SEQ. ID NO. 1)

or a hydrate, isostere, or pharmaceutically acceptable salt thereof wherein

P$_4$ is Ala, bAla, Leu, Ile, Val, Nva, bVal, Nle or a bond;
P$_3$ is Ala, bAla, Leu, Ile, Val, Nva, bVal, Nle or an N-methyl derivative, Pro, Ind, Tic or Tca, or Lys substituted on its epsilon amino group with a morpholino-B-group or Orn substituted on its delta amino group with a morpholino-B-group;
P$_2$ is Pip, Aze, Pro(4-OH), Pro(4-OAc) or Pro(4-OBz1);
R$_1$ is a side chain of Ala, Leu, Ile, Val, Nva or bVal;
X is —CF$_3$, —CF$_2$H, —CFH$_2$, —C(=O)Y, —C(=O)P$_2$'-Y, —CF$_2$C(=O)P$_2$'-Y, —CF$_2$CH(R$_1$')C(=O)P$_2$'-Y, —CF$_2$CH(R$_1$')NHC(=O)R$_3$, —CHFCH(R$_1$ )NHC(=O)R$_3$, —H, —C(=O)R$_3$, —CH(R$_1$)C(=O)P$_2$'-Y, —CF$_2$CF$_3$, —CF$_2$(CH$_2$)$_t$CH$_3$, —CF$_2$(CH$_2$)$_t$COOR4, —CHF(CH$_2$)$_t$CH$_3$, —CF$_2$(CH$_2$)$_t$CONHR$_4$, —CF$_2$(CH$_2$)$_t$CH$_2$OR$_4$, —CF$_2$(CH$_2$)$_v$CH=CH$_2$, —CH$_2$Cl or —C(=O)—C(=O)—Y;
R$_3$ is H, C$_{1-6}$ alkyl, phenyl, benzyl, cyclohexyl, cyclohexy-lmethyl;
R$_4$ is H or C$_{1-6}$ alkyl;
R$_1$' is a side chain of Ala, Leu, Ile, Val, Nva or bVal;
P$_2$' is a bond, Ala or Val;
Y is —NHR$_3$, OR$_3$;
t is 2, 3 or 4;
v is 1, 2 or 3;
K is hydrogen, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis((1-naphthyl)methyl)acetyl, —C(=O)N—(CH$_3$)$_2$,

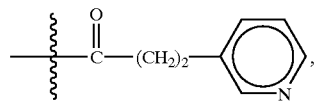

—A—$R_Z$ wherein

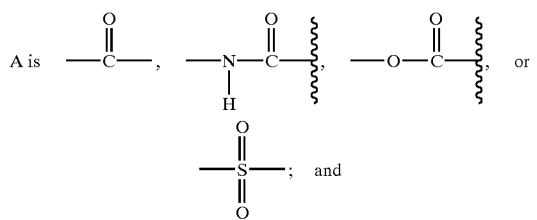

$R_Z$ is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro;

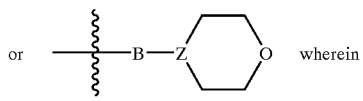

Z is N or CH, and
B is a group of the formulae

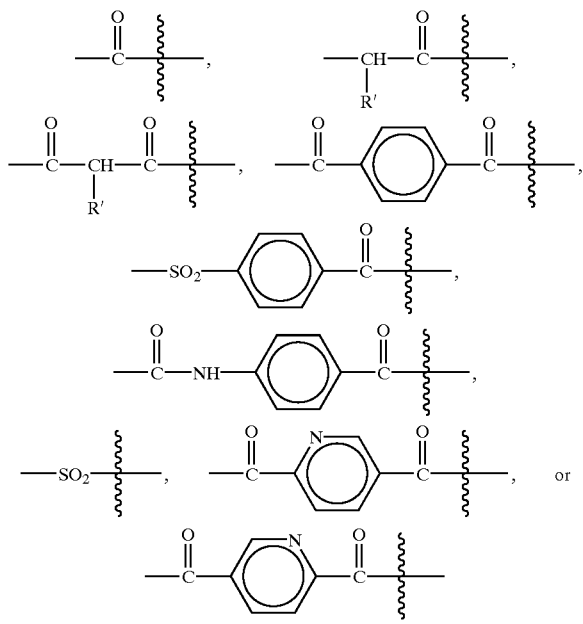

(the wavy line ⟩ being the attachment to the rest of the molecule, i.e., not to Z)
and wherein R' is hydrogen or a $C_{1-6}$ alkyl group; useful as inhibitors of elastase. The compounds of formula I exhibit an anti-inflammatory effect useful in the treatment of gout, rheumatoid arthritis and other inflammatory diseases, such as adult respiratory distress syndrome, septicemia, chronic bronchitis, inflammatory bowel disease, disseminated intravascular coagulation, cystic fibrosis, and in the treatment of emphysema.

DETAILED DESCRIPTION OF THE INVENTION

Isosteres of the compounds of formula I include those wherein (a) one or more of the a-amino residues of the $P_2$–$P_4$ substituents are in its unnatural configuration (when there is a natural configuration) or (b) when the normal peptidic amide linkage [—C(=O)NH—] is modified, such as for example, to form —$CH_2NH$— (reduced), —$COCH_2$— (keto), —CH(OH)$CH_2$—(hydroxy), —CH($NH_2$)$CH_2$— (amino), —$CH_2CH_2$— (hydrocarbon), —CH=CH— (alkene). Preferably a compound of the invention should not be in an isosteric form; particularly it is preferred that there be no modified peptidic amide group, but if there is, it is preferable to keep the isosteric modifications to a minimum.

A $C_{1-6}$ alkyl group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl.

The compounds of formua I can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy benzoic., and sulfonic acids such as methane sulfonic acid and 2-hydroxyethane sulfonic acid.

Those compounds of formula I wherein X is —C(=O)—C(=O)—Y, can exist in a hydrated or dehydrated form. Hydrates of these triketo compounds of formula I are much more chemically stable than are the dehydrated triketo compounds of formula I wherein X is —C(=O)—C(=O)—Y. For this reason, the hydrates are preferred and any reference in this specification and claims to a triketo compound should be taken to include reference to the corresponding hydrated form as context allows. Moreover, the compounds of this invention are expected to be in the hydrated form under normal physiological conditions.

Each α-amino acid has a characteristic "R-group", the R-group being the side chain, or residue, attached to the α-carbon atom of the a-amino acid. For example, the R-group side chain for glycine is hydrogen, for alanine it is methyl, for valine it is isopropyl. (Thus, throughout this specification, the $R_1$ moiety is the R-group for each indicated α-amino acid). For the specific R-groups or side chains of the α-amino acids reference to A. L. Lehninger's text on Biochemistry (see particularly Chapter 4) is helpful.

The natural amino acids, with the exception of glycine, contain a chiral carbon atom. Unless otherwise specifically indicated, the preferred compounds are the optically active amino acids of the L-configuration; however, applicants contemplate that the amino acids of the formula I compounds can be of either the D- or L-configurations or can be mixtures of the D- and L-isomers, including racemic mixtures. The recognized abbreviations for the α-amino acids are set forth in Table I.

TABLE I

| AMINO ACID | SYMBOL |
|---|---|
| Alanine | Ala |
| Isoleucine | Ile |
| Leucine | Leu |
| Lysine | Lys |
| Proline | Pro |
| Valine | Val |
| Norvaline | Nva |
| Norleucine | Nle |
| 1-Naphthylalanine | Nal (1) |
| 2-Indolinecarboxylic acid | Ind |
| beta-Alanine | bAla |
| beta-Valine | bVal |
| Methionine | Met |
| 1,2,3,4-Tetrahydro-3-isoquinoline carboxylic acid | Tic |
| Thiazolidine-4-carboxylic acid | Tca |
| Ornithine | Orn |
| Pipecolinic acid | Pip |
| Azetidine carboxylic acid | Aze |
| 4-Hydroxyproline | Pro(4-OH) |
| 4-Acetoxyproline | Pro(4-OAc) |
| 4-Benzyloxyproline | Pro(4-OBzl) |

As with any group of structurally related compounds which possesses a particular generic utility, certain groups and configurations are preferred for compounds of formula I in their end-use application.

With respect to the substituent $P_4$, compounds of formula I wherein $P_4$ is Ala or a bond, are preferred. Compounds of formula I wherein $P_4$ is a bond are particularly preferred.

With respect to the substituent $P_3$, compounds of formula I wherein $P_3$ is Ile, Val or Ala, are preferred. Compounds of formula I wherein $P_3$ is Val are particularly preferred.

As for substituent $R_1$, compounds of formula I wherein $R_1$ is —CH(CH$_3$)$_2$ or —CH$_2$CH$_2$CH$_3$, being the characteristic "R-groups" of the amino acids Val and Nva, respectively, are preferred. Compounds of formula I wherein $R_1$ is —CH(CH$_3$)$_2$ are particularly preferred.

With respect to the substiuent X, compounds of formula I wherein X is —CF$_2$CF$_3$, —CF$_3$, —CF$_2$(CH$_2$)$_t$CH$_3$, —CF$_2$(CH$_2$)$_t$COOR$_4$, —CHF(CH$_2$)$_t$CH$_3$, —CF$_2$(CH$_2$)$_t$CONHR$_4$, —CF$_2$(CH$_2$)$_t$CH$_2$OR$_4$, or —CF$_2$(CH$_2$)$_v$CH═CH$_2$, are preferred. Compounds of formula I wherein X is —CF$_2$CF$_3$ are particularly preferred.

With regard to the substituent K, compounds of formula I wherein K is benzoyl, t-butyloxycarbonyl, carbobenzyloxy, isovaleryl, —C(═O)N(CH$_3$)$_2$,

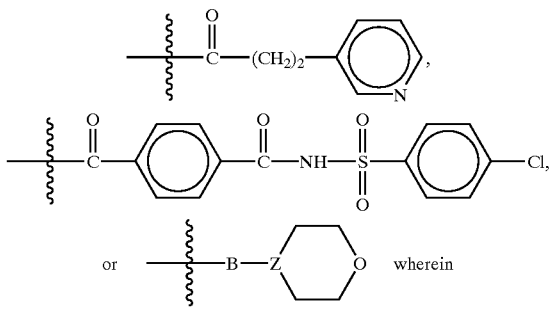

or wherein

Z is N and B is a group of the formulae

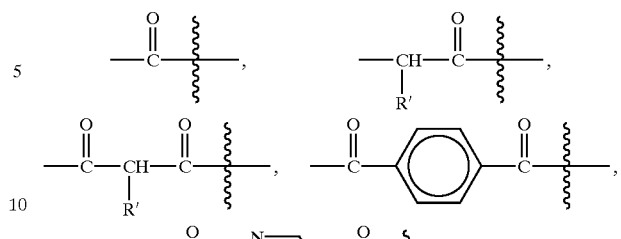

and wherein R' is hydrogen or a $C_{1-6}$ alkyl group are preferred. Compounds of formula I wherein K is

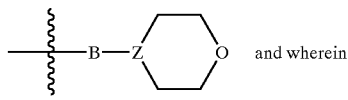 and wherein

Z is N and B is a group of the formulae

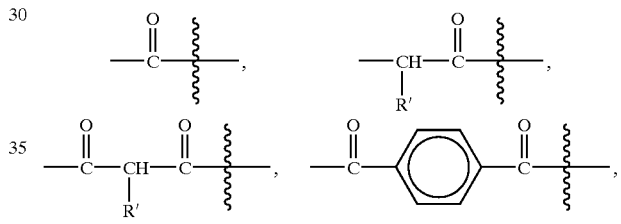

and wherein R' is hydrogen or a $C_{1-6}$ alkyl group are particularly preferred.

Specific examples of preferred compounds include:

N-[4-(4-morpholinylcarbonyl)benzoyl]-L-valyl-N'-[3,3,4,4,4-pentafluoro-1-(1-methylethyl)-2-oxobutyl]-L-2-azetamide;

N-[4-(4-morpholinylcarbonyl)benzoyl]-L-valyl-N'-[3,3,4,4,4-pentafluoro-1-(1-methylethyl)-2-oxobutyl]-D,L-2-pipecolinamide;

N-[4-(4-morpholinylcarbonyl)benzoyl]-L-valyl-N'-[3,3,4,4,4-pentafluoro-1-(1-methylethyl)-2-oxobutyl]-trans-4-hydroxyprolinamide;

N-[4-(4-morpholinylcarbonyl)benzoyl]-L-valyl-N'-[3,3,4,4,4-pentafluoro-1-(1-methylethyl)-2-oxobutyl 1-trans-4-acetoxyprolinamide;

N-[4-(4-morpholinylcarbonyl)benzoyl]-L-valyl-N'-[3,3,4,4,4-pentafluoro-1-(1-methylethyl)-2-oxobutyl 1-trans-4-benzyloxyprolinamide.

In general, the compounds of formula I may be prepared using standard chemical reaction analogously known in the art and as depicted in Scheme A.

Scheme A

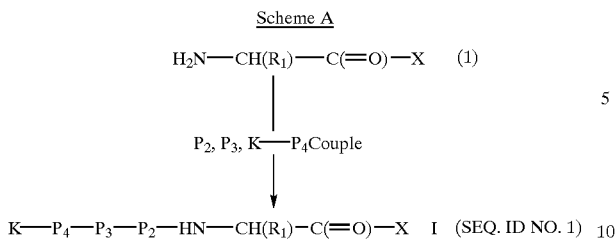

$$H_2N-CH(R_1)-C(=O)-X \quad (1)$$

$$P_2, P_3, K-P_4 \text{ Couple}$$

$$K-P_4-P_3-P_2-HN-CH(R_1)-C(=O)-X \quad I \quad (\text{SEQ. ID NO. 1})$$

Scheme A provides a general synthetic scheme for preparing the compounds of formula I.

The $P_2$, $P_3$ and $K-P_4$ groups can be linked to the free amino group of the amino acid derivative of structure (1). Note that structure (1) represents the $P_1$ moiety wherein the free carboxylic acid group has been substituted with an "X" moiety as defined above. The $P_2$, $P_3$ and $K-P_4$ can be linked to the unproptected, free amino compound ($P_1$-X) by well known peptide coupling techniques. Furthermore, the $P_1$, $P_2$, $P_3$ and $K-P_4$ groups may be linked together in any order as long as the final compound is $K-P_4-P_3-P_2-P_1-X$. For example, $K-P_4$ can be linked to $P_3$ to give $K-P_4-P_3$ which is linked to $P_2-P_1-X$; or $K-P_4$ linked to $P_3-P_2$ then linked to an appropriately C-terminal protected Pi and the C-terminal protecting group converted to X.

Generally, peptides are elongated by deprotecting the α-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme A, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the aldehyde group to form a bond which is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated. For compounds of formula I wherein X is H, a linker compound may also be used in the reaction of Scheme A to link a resin to the aldehyde funcationlity of the amino acid derivative of structure (1) wherein X is H. Examples of suitable linker compounds are

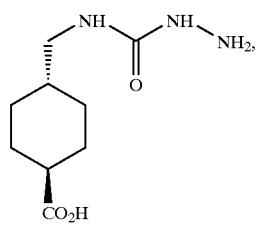

L1

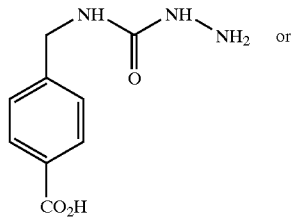

L2

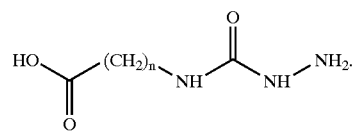

L3

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides; Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The α-carboxyl group of the C-terminal residue is usually protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid to be coupled to the growing peptide chain must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonxyls, 1-(p-biphenyl)-1-methylethoxycarbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycaronbyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc, preferably Boc. Many amino acid derivaties suitably protected for peptide synthesis are commercially available.

The α-amino group protecting group of the newly added amino acid residue is cleaved prior to the coupling of the next amino acid. When the Boc group is used, the methods of choice are trifluoroacetic acid, neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethlformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the a-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine and benzyl (Bzl) ether can be used to protect the hydroxy containing side chains of amino acids such as Ser or Thr.

When Fmoc is chosen for the α-amine protection, usually tert-butyl based protecting groups are acceptable. For instance, Boc can be used for lysine, tert-butyl ether for serine and threonine and tert-butyl ester for glutamic acid.

Once the elongation of the peptide is completed all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additivies such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using solution of trifluoroacetic acid and various additives such as anisole, etc.

For those compounds of formula I wherein X is H, the peptide compound of formula I may be cleaved from the linker compound and resin with aqueous acid/formaldehyde.

Alternatively, the compounds of formula I may be prepared using standard chemical reaction analogously known in the art and as depicted in Scheme B

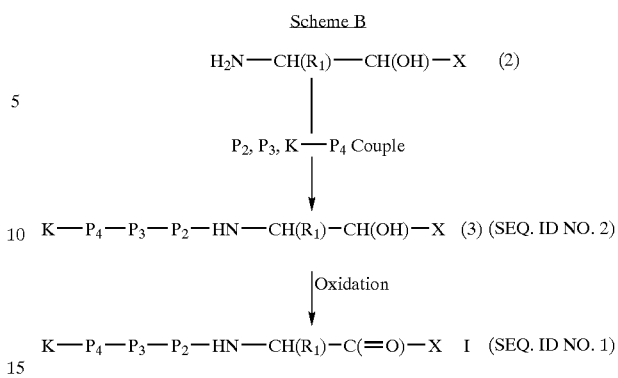

Scheme B provides an alternative general synthetic scheme for preparing the compounds of formula I.

The $P_2$, $P_3$ and K—$P_4$ groups can be linked to the free amino group of the amino alcohol derivative of structure (2) as described previously in Scheme A to give the peptido alcohol of structure (3).

The alcohol functionality of the peptido alcohol of structure (3) is then oxidized by techniques and procedures wellknown and appreciated by one of ordinary skill in the art, such as a Swern Oxidation using oxalyl chloride and dimethylsulfoxide, to give the compounds of formula I.

Starting materials for use in Schemes A and B are readily available to one of ordinary skill in the art. For example, amino acids $P_2$, $P_3$ and K—$P_4$ wherein K is hydrogen are commercially available and the linker compound of structure (L1) is described in J. Am. Chem. Soc., 114, 3157–59 (1992). In addition, substituted amino acids K—$P_4$ wherein K is acetyl, succinyl, benzoyl, t-butyloxycarbonyl, carbobenzyloxy, tosyl, dansyl, isovaleryl, methoxysuccinyl, 1-adamantanesulphonyl, 1-sdamantaneacetyl, 2-carboxybenzoyl, phenylacetyl, t-butylacetyl, bis [(1-naphthyl)-methyl]acetyl or —A—$R_Z$ wherein
A is

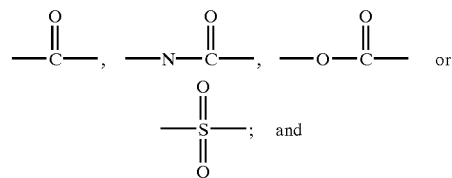

$R_Z$ is an aryl group containing 6, 10 or 12 carbons suitably suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto are described in European Patent Application OPI No. 0363284, Apr. 11, 1990.

Starting amino compounds of structure (1) are readily available to one of ordinary skill in the art. For example, certain protected amino compounds of structure (1) wherein X is H are well known in the literature and are also described in European Patent Application OPI No. 0275101, Jul. 20, 1988 and in European Patent Application OPI No. 0363284, Apr. 11, 1990. In addition, amino compounds of structure (1) wherein X is —$CF_3$, —$CF_2(CH_2)_tCH_3$, —$CF_2(CH_2)_tCOOR_4$, —$CF_2(CH_2)_tCONHR_4$, —$CF_2(CH_2)_tCH_2OR_4$, —$CF_2CF_3$, and —$CF_2(CH_2)_tCH=CH_2$ are described in European Patent Application OPI No. 0503203, Sep. 16, 1992. Amino compounds of structure (1) wherein X is —$CF_3$, —$CF_2H$, —C(=O)—Y, —$CF_2CH(R_{1'})$—C(=O)$P_{2'}$—Y and —C(=O)—$P_{2'}$—Y are described in European Patent Application OPI No. 0195212, Sep. 24, 1986. Amino compounds of structure (1) wherein X is —$CF_2CH(R_{1'})$NHC(=O)$R_3$ are described in OPI No. 0275101, Jul. 20, 1988 and amino comounds of structure (1) wherein X is —CHFCH($R_{1'}$)NHC(=O)$R_3$ may be prepared by analogous procedures using bromo-fluroacetic acid, ethyl ester in place of bromo-difluroacetic acid, ethyl ester. Amino compound of structure (1) wherein X is —$CFH_2$ are described in *Biochem. J.* (1987), 241, 871–5, *Biochem. J.* (1986), 239, 633–40 and U.S. Pat. No. 4,518,528, May 21, 1985. Amino compounds of structure (1) wherein X is —$CO_2R_3$, C(=O)—$R_3$ and —CH($R_1$)—C(=O)$P_{2'}$—Y are described in European Patent Application OPI No. 0363284, Apr. 11, 1990. Amino compounds of structure (1) wherein X is —$CF_2CH(R_{1'})$NHC(=O)—$R_3$ are described in European Patent Application OPI No. 0275101, Jul. 20, 1988. In addition, amino compounds of structure (15) wherein X is —$CF_2CF_3$ are described in European Patent Application OPI No. 0410411, Jan. 30, 1991. The linker compound trans-4-(aminomethyl)-cyclohexanecarboxylic acid, benzyl ester used in synthesis of compounds of formula I wherein X is H is prepared from the corresponding acid as described in *J. Am. Chem. Soc.* 1992, 114, 3156–3157.

In addition, other starting materials for use in Schemes A and B may be prepared by the following synthetic procedures which are well known and appreciated by one of ordinary skill in the art.

Substituted amino acids K—$P_4$ of structure wherein K is

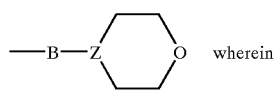 wherein

Z is N or CH, and
B is a group of the formulae

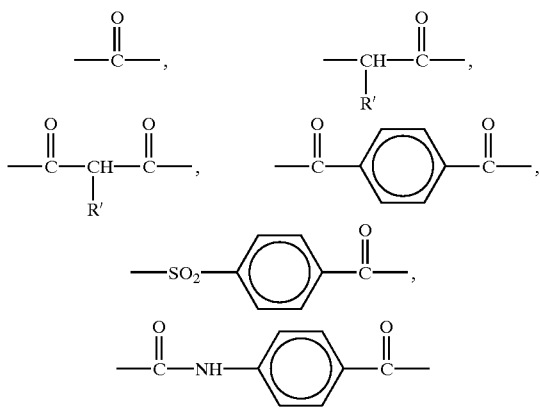

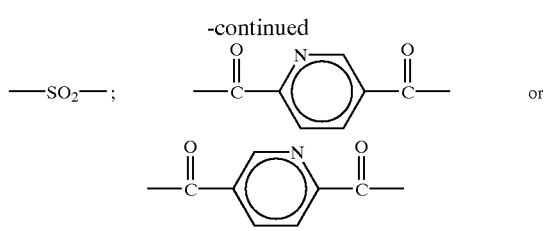

wherein R' is hydrogen or a $C_{1-6}$ alkyl group are prepared using standard chemical reactions analogously known in the art.

The procedure for preparing the substituted amino acids K—$P_4$ wherein K is

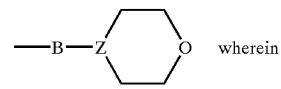 wherein

B is a —C(=O)— is outlined in Scheme C wherein $P_4$ and Z are as previously defined or are the functional equivalents of these groups.

Scheme C

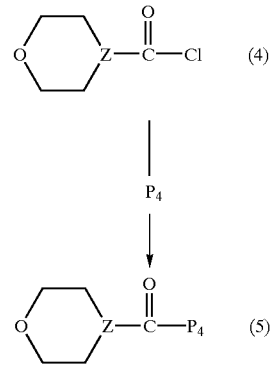

Specifically the amino acids K—$P_4$ wherein K is

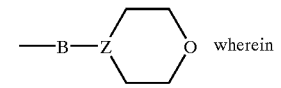 wherein

B is a —C(=O)— are prepared by coupling of the amino acid K—$P_4$ wherein K is hydrogen with an acid chloride of structure (4) in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride of structure (4), to a solution of the amino acid K—$P_4$ wherein K is hydrogen. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The N-protected amino acids K—P$_4$ wherein K is

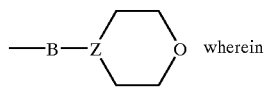 wherein

B is a —C(=O)— can be isolated from the reaction mixture by any appropriate techniques such as by chromatography on silica gel.

The substituted amino acids K—P$_4$ wherein K is

 wherein

B is other than a —C(=O)— can be prepared analogously, merely by substituting the appropriate intermediate

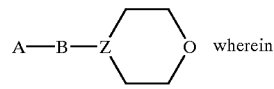 wherein

B is other than a —C(=O)— and A is Cl or OH (the corresponding acid, acid chloride or sulphonyl chloride) for the compound of structure (5) in Scheme C.

The acid chloride of structure (4) and the appropriate intermediate of formula

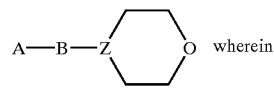 wherein

B is other than a —C(=O)— and A is Cl or OH (the corresponding acid, acid chloride or sulphonyl chloride) are commercially available or may be readily prepared by techniques and procedures well known and appreciated by one of ordinary skill in the art.

For example, the appropriate intermediates of formula

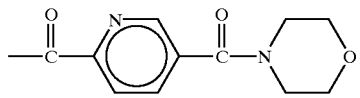

may be prepared as outlined in Scheme D wherein all substituents are as previously defined.

Scheme D

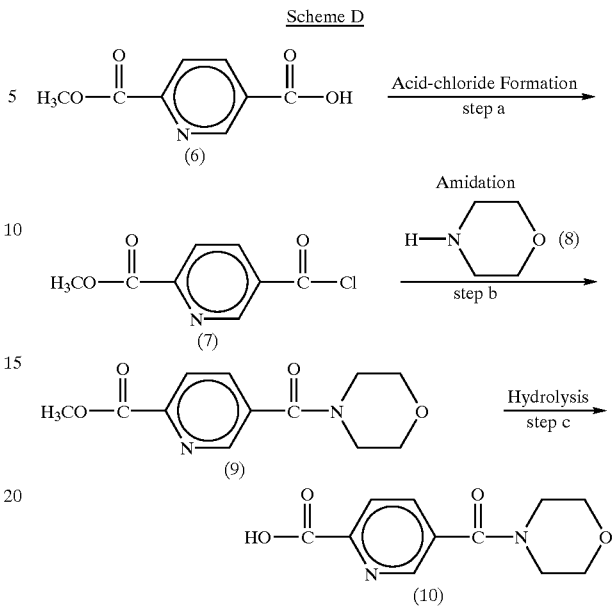

Scheme D provides a general synthetic procedure for preparing the appropriate intermediates of formula

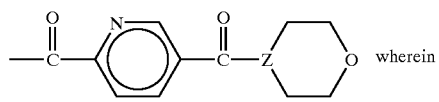 wherein

Z is as previously defined.

In step a, the carboxylic acid functionality of the appropriate 2,5-pyridinedicarboxylic acid, 2-methyl ester (6) (*Nippon Kagaku Zasshi*, 1967, 88, 563) is converted to its acid chloride using techniques and procedures well known and appreciated by one of ordinary skill in the art, such as thionyl chloride, to give the corresponding 6-carbomethoxynicotinoyl chloride (7).

In step b, the acid chloride (7) is amidated with morpholine (8) by techniques and procedures well known and appreciated by one of ordinary skill in the art to give the corresponding 5-(morpholine-4-carbonyl)-2-pyridinecarboxylic acid, methyl ester (9).

In step c, the methyl ester functionality (9) is hydrolyzed by techniques, and procedures well known and appreciated by one of ordinary skill in the art, with for example, lithium hydroxide in methanol, to give 5-(morpholine-4-carbonyl)-2-pyridine carboxylic acid (10).

In addition, the appropriate intermediate of formula

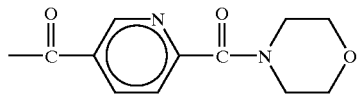

may be prepared as outlined in Scheme E wherein all substituents are as previously defined.

Scheme E

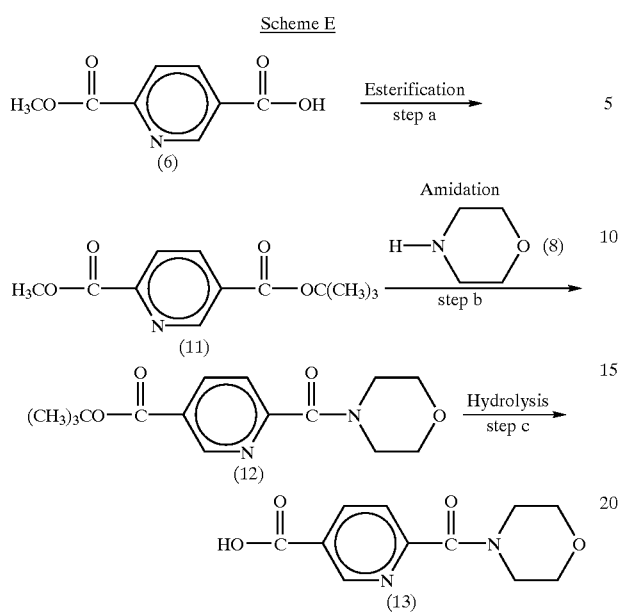

Scheme E provides a general synthetic procedure for preparing the appropriate intermediates of formula

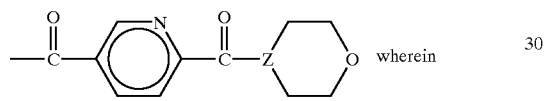 wherein

Z is as previously defined.

In step a, the free carboxylic acid functionality of 2,5-pyridinedicarboxylic acid, 2-methyl ester (6) (*Nippon Kagaku Zasshi*, 1967, 88, 563) is converted to its t-butyl ester using techniques and procedures well known and appreciated by one of ordinary skill in the art, such as the t-butyl alcohol adduct of dicyclohexylcarbodiimide (*Synthesis*, 1979, 570), to give the corresponding 2,5-pyridinedicarboxylic acid, 2-methyl ester, 5-t-butyl ester (11).

For example, the 2,5-pyridinedicarboxylic acid, 2-methyl ester (6) is combined with a molar excess of the t-butyl alcohol adduct of dicyclohexylcarbodiimide in an appropriate organic solvent, such as methylene chloride. The reaction is typically conducted at a temperature range of from 0° C. to room temperature and for a period of time ranging from 2–24 hours. The 2,5-pyridinedicarboxylic acid, 2-methyl ester, 5-t-butyl ester (11) is isolated from the reaction mixture by standard extractive methods as is known in the art and may be purified by crystallization.

In Step b, the methyl ester functionality of (11) is amidated with morpholine (8) to give the corresponding 6-(morpholine-4-carbonyl)nicotinic acid, t-butyl ester (12). For example, the 2,5-pyridinedicarboxylic acid, 2-methyl ester, 5-t-butyl ester (11) is contacted with a molar excess of morpholine in an appropriate organic solvent, such as tetrahydrofuran. The reaction is typically conducted at a temperature range of from room temperature to reflux and for a period of time ranging from 5 hours to 3 days. The 6-(morpholine-4-carbonyl)nicotinic acid, t-butyl ester (12) is isolated from the reaction mixture by standard extractive methods as is known in the art and may be purified by crystallization.

In step c, the t-butyl ester functionality of (12) is hydrolyzed, with for example, HCl in nitromethane, to give the corresponding, 6-(morpholine-4-carbonyl)nicotinic acid (13).

Amino compounds of structure (1) wherein X is —C(=O)—C(=O)—Y may be prepared by techniques and procedures well known by one of ordinary skill in the art.

For example, amino compounds of structure (1) wherein X is —C(=O)—C(=O)—Y may be prepared as described in Scheme F wherein all substituents are as previously defined.

Scheme F

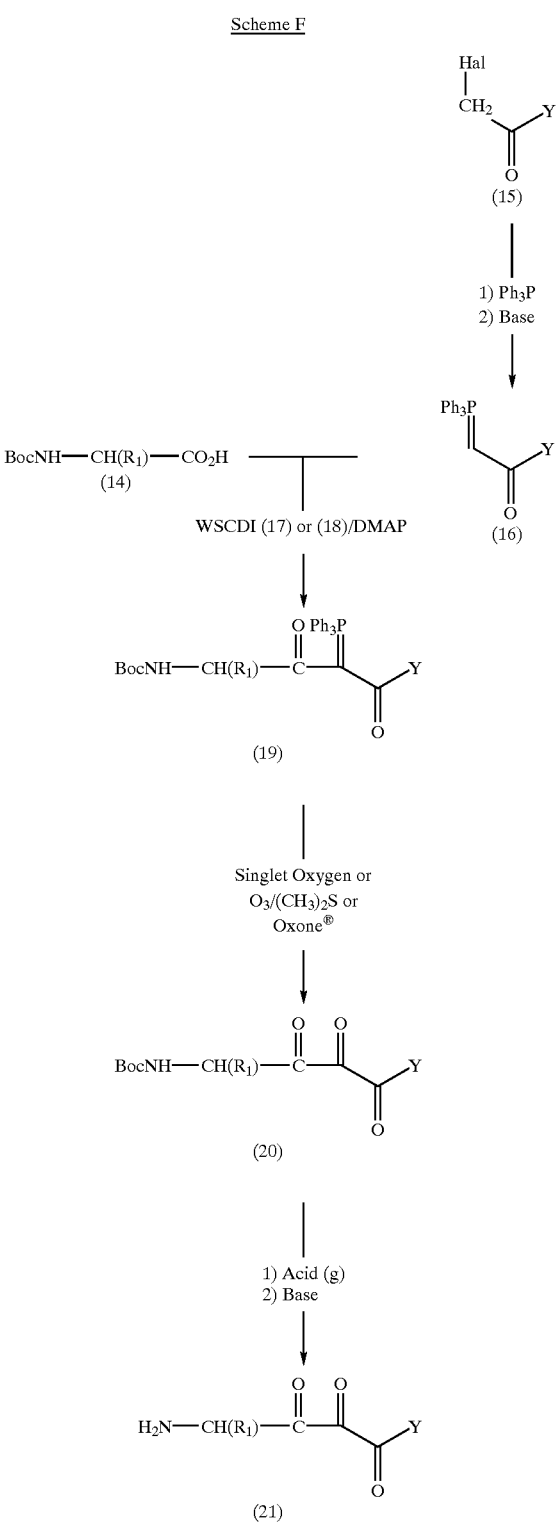

Specifically, the amino compounds of structure (1) wherein X is —C(=O)—C(=O)—Y can be prepared, as illustrated in scheme F, by treatment of the appropriate N-Boc protected tricarbonyl compound (20) with an appropriate acid, such as hydrogen chloride in ethyl acetate or nitromethane or trifluoroacetic acid neat or as a solution in methylene chloride, followed by generation of the free base (21) using an appropriate base.

Intermediate (20) is generated from ylide (19) by treatment with (a) ozone and dimethyl sulfide or (b) singlet oxygen or (c) Oxone®. The ozonolysis reaction can be conveniently performed by, for example, bubbling an excess of ozone through a cooled solution of the appropriate ylide of structure (20). Suitable solvents include any nonreactive solvent in which the ylide of structure (20) is soluble, for example, alkyl esters of simple alkanoic acids such as ethyl acetate; the chlorinated hydrocarbons such as carbon tetrachloride, chloroform, 1,2-dichloroethane, 1,1,2,2-tetrachloroethane, and methylene chloride; the aromatic hydrocarbons such as benzene, toluene, and xylene; a chlorinated aromatic such as 1,2,4-trichlorobenzene and o-diclorobenzne; or an ethereal solvent such as diethyl ether, tetrahydrofuran (THF), and 1,4-dioxane. Methylene chloride is preferred.

The temperature of the ozonolysis reaction mixture can be any temperature conductive to the reaction, typically from about −78° C. to about 0° C. preferably from about −78° C. to about −35° C., and most preferably about −70° C. The time of the reaction will vary depending on the ylide, the conentration of the reactants, the temperature and other factors. Conveniently, ozone is bubbled into the reaction mixture until the solution turns blue indicating an excess of ozone.

The ozonide is then treated with an excess of a reducing agent such as zinc metal or preferably dimethylsulfide. Compound (20) is isolated as the hydrate from the reaction mixture in any convenient manner, typically by solvent removal (via evaporation). Purification may be accomplished by, for example, flash chromatography (Still, W. C.; Kahn, M.; Mitra, A.; *J. Org. Chem.* 1978, 43, 2923).

Oxone® may be used in place of ozone whe a milder and more selective reagent is desired. Typically, ylide (19) is treated with 1.5 equivalents of Oxone® in THF—$H_2O$ and the resultant hydrated tricarbonyl is isolated from the reaction mixture.

Oxidations utilizing singlet oxygen are well known. More specifically, singlet oxygen oxidation of an ylide to produce a tricarbonyl ester has been reported by H. Wasserman et al., *J. Amer. Chem. Soc.*, 11, 371 (1989). Singlet oxygen can be generated by dye-sensitized excitation of oxygen. Suitable dyes include Rose Bengal, Eosin Y and methylene blue. Other sensitizers include inaphthalenethiophene. Typically, Rose Bengal and Eosin Y are attached to a basic anion-exchange resin and methylene blue is attached to an acidic cation-exchange resin. Excitation is accomplished with a UV lamp such as a tungsten-iodine lamp. Suitable solvents are any solvents which promote and do not interfere with the desired reaction. Such solvents include the aromatic hydrocarbons such as benzene and toluene; hydrocarbons such as hexane; ethereal solvents such as diethyl ether, tetrahydrofuran (THF), 1,4-dioxane; chlorinated hydrocarbons such as dichloromethane and chloroform; and carbon disulfide. Mixtures are operable. The temperature of the reaction mixture can be any suitable temperature from about −78° C. to about 30° C. typically from about −78° C. to −50° C. The time of the reaction will vary depending on the reactant, the solvent, concentrations, and temperature and can be from about 1 minute to about 2 hours. Purification and isolation can by by those methods desrbied above for specification and isolation of product from ozonolysis reaction mixture.

The N-Boc protected ylide of structure (19) is prepared by coupling of the N-Boc protected amino acid of structure (14) with the phosphonium ylide of structure (16) using a water-soluble carbodiimide (WSCDI) such as 1-(3-dimethylaminopropyl)-3-ethylcarbodiimide hydrochloride (17) or 1-(3-dimethylaminopropyl)-3-ethylcarbodiimide methiodide (18) in the presence of 4-dimethylaminopyridine (DMAP) in a suitable solvent such as THF or dichloromethane. The reaction will require from about 30 minutes to about 12 hours, typically about 2 to 3 hours, depending on the amino acid, the ylide, the solvent(s), and the temperature which can be from about −15° C. to about 60° C., but typically at 0° C. Isolation and purification is accomplished by filtering the reaction mixture to remove solid products and subseqently chromatographing the filtrate, for example, on silica gel.

The phosphorous ylide, Wittig reagent, of structure (16) is prepared from the corresponding α-halocarboxylic acid derivative of structure (15) in the usual manner, that is, by reacting the α-halo ester with a tertiary phosphine such as triphenylphosphine to yield a phosphonium salt. When treated with a strong base such as an organolithium compound, for example, lithium diisopropylamide (LDA), sodium hydride, or sodium amide, the acidic proton is removed and the desired ylide is formed. Suitable solvents used in forming the Wittig reagent include any nonreactive solvent, for example, the aromatic hydrocarbons such as benzene or toluene, the chlorinated hydrocarbons such as carbon tetrachloride, chloroform, or methylene chloride, or the ethereal solvents such as diethyl ether or THF.

The reaction can conveniently be performed at from about 0° C. to about 60° C., typically at room temperature, that is about 25° C. The halo group of the a-halo ester is preferably a bromo group, but can be a chloro or iodo group or can by any good leaving group which forms a stable phosphonium salt such as a mesylate or tosylate group.

In addition, amino compounds of structure (1) wherein X is —CHF$(CH_2)_t$$CH_3$ may be prepared as described in Scheme G wherein all substituents are as previously defined

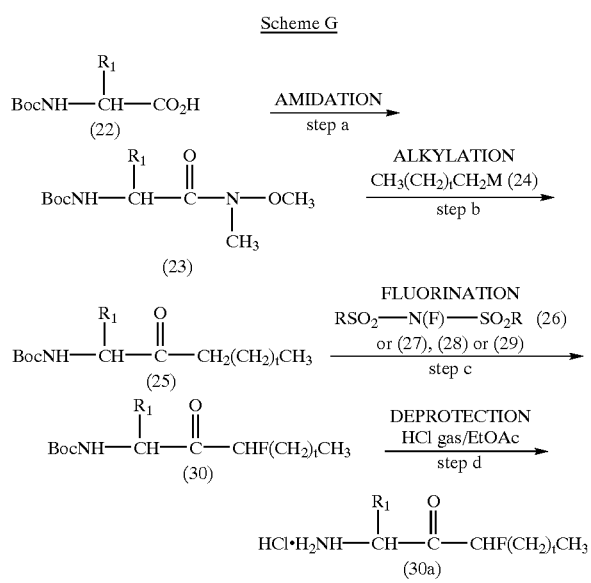

Scheme G

-continued

R = CF₃, Phenyl
M = Li, Mg

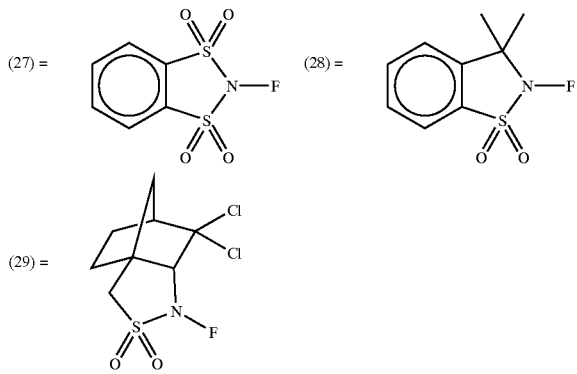

Scheme G provides a general synthetic procedure for preparing the amino compounds of structure (1) wherein X is —CHF(CH₂)ₓCH₃. In Scheme G, all substituents are as previously defined unless otherwise indicated.

In step a, the appropriate acid of structure (22) is amidated with N-methyl-N-methoxyamine by techniques and procedures well known and appreciated by one of ordinary skill in the art, such as a coupling reaction using 1,3-dicyclohexylcarbodiimide (DCC) and 1-hydroxybenzotriazole (HOBT) to give the corresponding amide of structure (23).

In step b, the appropriate amide of structure (23) is alkylated with the appropriate alkyl metal compound of structure (24) to give the corresponding keto compound of structure (25).

For example, the appropriate amide of structure (23) is treated with the alkyl metal compound of structure (24) in a suitable aprotic, anhydrous organic solvent wuch as tetrahydrofuran or diethyl ether. The reaction is typically conducted at a temperature range of from −78° C. to −40° C. and for a period of time ranging from 30 minutes to 5 hours. The corresponding keto compound of structure (25) is recovered from the reaction zone by extractive methods as is known in the art and may be purified by chromatography.

In step c, the appropriate keto compound of structure (25) is fluorinated with the N-fluorosulfonimide compound of structure (26), or the alternative fluorination reagents (27), (28) or (29) to give the protected amino compounds of structure (30) which is the amino compound of structure (1) in which the amino terminal group is substituted with a Boc group and X is —CHF(CH₂)ₓCH₃.

For example, the appropriate keto compound of structure (25) is treated with an appropriate non-nucleophilic base, such as lithium diisopropylamide in a suitable anhydrous aprotic organic solvent, such as tetrahydrofuran at a temperature range of from −78° C. to −40° C. and for a period of time ranging from 5 minutes to 2 hours. The reaction mixture is then treated with the N-fluorosulfonimide compound of structure (25) and the reaction conducted at a temperature range of from −78° C. to −40° C. and for a period of time ranging from 30 minutes to 10 hours. The N-t-Boc protected amino compounds of structure (1) wherein X is —CHF(CH₂)ₓCH₃ is recovered from the reaction zone by extractive methods as is known in the art and may be purified by chromatography.

Alternate routes for the preparation of compounds of structure (1) wherein X=—CF₂CF₃, is shown in scheme H.

The required starting material defined by compound (31) is readily available either commercially or by applying known prior art principles and techniques. The term "Pg" refers to a suitable protecting group as more fully defined previously.

In Scheme H, step a the protected amino acid (31) is transformed into the hydroxamate (32). This amidation can be performed utilizing a coupling reaction as between two amino acids using the protected amino acid (31) and the N-alkyl O-alkylhydroxylamine. The standard coupling reaction can be carried out using standard coupling procedures as described previously for the coupling between two amino acids to provide the hydroxamate (32).

In step b, the protected hydroxamate (32) is transformed into the protected pentafluoroketone (34) (or (35)]. This reaction can be performed utilizing a reaction of the type described in the following reference M. R. Angelastro, J. P Scheme H

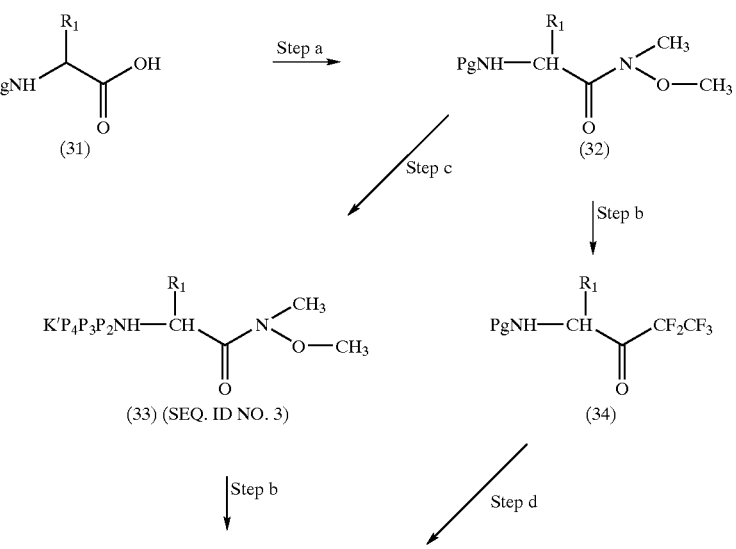

-continued

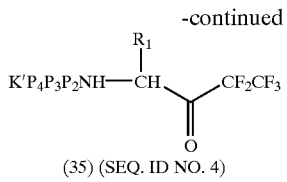

(35) (SEQ. ID NO. 4)

Burkhart, P. Bey, N. P. Peet, *Tetrahedron Letters*, 33 (1992), 3265–3268.

In step c, the hydroxamate (32) is deprotected under conditions well known in the art as described by T. H. Green "Protection Groups in Organic Synthesis", John Wiley and Sons, 1981, Chapter 7, to provide the deprotected hydroxamate. The deprotected hydroxamate is elongated by coupling the next suitably protected amino acid through a peptide linkage using the methods previously described, or by condensation of fragments, or combination of both processes to provide the elongated peptide (33).

In step d, the ketone (34) is deprotected under conditions as previously described. The deprotected ketone (34) is elongated by coupling the next suitably protected amino acid through a peptide linkage using the methods previously described, or by condensation of fragments, or combination of both processes to provide the elongated ketone (35).

Alternatively, the corresponding N-protected amino acid ester of (31) [i.e. PgNH—CH($R_1$)C(=O)$OR_2$, (32a), wherein $R_2$ and Pg are as defined above] can be substituted for the hydroxamate (32). The corresponding protected amino acid esters of (31) are commercially available or easily synthesized from (31) by procedures well known by one of ordinary skill in the art. In step b, the amino acid ester (32a), is transformed into the N-protected pentafluoroketone (34) (or (35)] in a manner directly analogous to that used for the corresponding hydroxamate. Steps c and d would be the same as those employed when utilizing the hydroxamate (32).

For example, the amino acid ester (32a) may be reacted with a suitable perfluorinating agent, such as, from 4–8 equivalents of perfluoroethyl iodide or perfluoroethyl bromide. Said reaction is carried out in the presence of a suitable alkali metal base, for example from 4–8 equivalents of MeLi/LiBr in an appropriate anhydrous solvent (or mixed solvents), such as ether, THF, or toluene. Other examples of suitable alkali metal bases include t-BuLi, EtMgBr, PhMgBr, n-BuLi, and the like. The reaction is carried out at reduced temperature of from −100° C. to 0° C., preferably from −30° C. to −80° C., to provide the protected perfluoropropyl amino ketone and the protected perfluorobutyl amino ketone, respectively. Steps c and d would be the same as those employed when utilizing the hydroxamate (32).

Alternatively, the N-protected amino acid ester (32a) could first be deprotected and coupled with a suitably N-protected peptide in the presence of a suitable coupling agent and in the presence of an appropriate coupling solvent. The subsequently formed N-protected peptide ester [$KP_4P_3P_2$NH—CH($R_1$)C(=O)$OR_2$, (33a)] would then be per-fluorinated in a manner directly analogous to that used for the corresponding hydroxamate. Steps c and d would be the same as those employed when utilizing the hydroxamate (33).

All of the amino acids employed in the synthesis of Formula I are either commercially available or are easily synthesized by one skilled in the pertinent art. For example, the amino acid derivative Pro(4-Ac) defined in $P_2$ can be made by esterifying a Pro residue by utilizing techniques well-known by one of ordinary skill in the art.

The following examples present typical syntheses as described in Schemes A through H. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; and "μM" refers to micromolar; "DME" refers to 1,2-dimethoxyethane; "DCC" refers to dicyclohexylcarbodiimide; "h" refers to hour; "DMF" refers to N,N'-dimethylformamide; "conc" refers to concentrated; "NMM" refers to N-methylmorpholine, "in vacuo" refers to removal of solvent under reduced pressure.

EXAMPLE 1

Preparation of N-[4-(4-morpholinylcarbonyl)benzoyl]-L-valyl-N'-[3,3,4,4,4-pentafluoro-1-(1-methylethyl)-2-oxobutyl]-L-2-azetamide

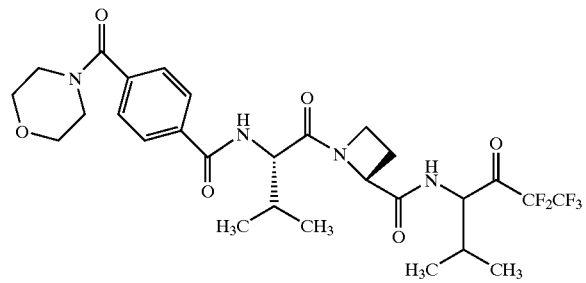

MDL 104,238 a) Preparation of N-[(1,1-Dimethylethoxy)carbonyl]-L-valyl-succinimide

To a cooled (icebath) stirred solution of BOC—L-valine (4.56 g, 0.021 mol), and N-hydroxysuccinimide (2.41 g, 0.021 mol) in DME (50 mL) was added DCC (4.75 g, 0.023 mol). The reaction was stirred for 6 h at 5° C. and then left to stand in the refrigerator over night. The reaction was then cold filtered, washing with $Et_2O$, and conc to yield a solid which was crystallized from EtOAc/hexane to give the desired product as a white crystalline sold (4.59 g, 69.5%): mp 123–124° C.; $^1$H NMR (300 MHz, $CDCl_3$) δ 5.00–4.95 (d, 1H, J=9.3 Hz), 4.62 (dd, 1H, J=4.97 Hz), 2.85 (s, 4H), 2.75–2.44 (m, 1H), 1.45 (s, 9H), 1.25–0.90 (m, 6H); $^{13}$C NMR ($CDCl_3$) δ 168.6, 167.9, 155.1, 155.0, 80.4, 77.4, 77.2, 77.0, 76.6, 76.5, 57.0, 31.6, 31.1, 28.2, 28.1, 28.0, 27.99, 27.93, 25.5, 18.6, 17.3; MS (Cl/$CH_4$) m/z 315 (MH+), 299, 287, 259, 241, 215 (base peak), 173, 172, 145, 144, 116, 100, 72. Anal. Calcd. for $C_{14}H_{22}N_2O_6$: C, 53.49; H, 7.05; N, 8.91. Found: C, 53.67; H, 7.06; N, 8.81.

b) N-[(1,1,-dimethylethoxy)carbonyl]-L-valyl-L-2-azetidine Carboxylic Acid

To a stirred solution of (S)-(−)-2-azetidine carboxylic acid (1.0 g, 10 mmol) and $Et_3N$ (1.5 mL, 11 mmol) in DMF (30 mL) was added the product of part (a) (2.8 g, 9.0 mmol) and the reaction was heated to 120° C. for 2.5 h. Upon cooling, the reaction was conc in vacuo and the oily residue was dissolved in EtOAc and washed with 1N HCl (2×30 mL), dried (MgSO$_4$) and conc to give the desired product as a white foam (1.88 g, 65%); $^1$H NMR (300 MHz, CDCl$_3$) δ 9.15 (br s, 1H), 5.09 (d, 1H, J=8.8 Hz, NH), 5.00 (dd, 1H, J=9.2, 7.2 Hz, α-CH of Val), 4.43 (dd, 1H, J=7.0, 1.49 Hz), 4.17 (m, 1H), 3.94 (app t, 1H, J=8 Hz), 2.62 (m, 3H), 1.44 (s, 9H, tBu), 0.97 (d, 6H, J=6.7 Hz, 2×CH$_3$).

c) N-[(1,1-dimethylethoxy)carbonyl]-L-valyl-N'-[3,3,4,4,4-pentafluro-1-(1-methylethyl)-2-oxobutyl]-L-2-azetamide To a stirred solution of the product of part (b) (1.80 g, 6.0 mmol) and NMM (0.66 mL, 6.0 mmol) in dry CH$_2$Cl$_2$ (50 mL) at −20° C. under nitrogen was added dropwise isobutylchloroformate (0.79 mL, 6.0 mmol). After 20 min, 4-amino-1,1,1,2,2,-pentafluoro-5-methyl-3-hexanone hydrochloride (1.54 g, 6.0 mmol) (from European Patent Application OPI No. 0410411, publ. Jan. 30, 1991) was added, immediately followed by another equivalent of NMM (0.66 mL, 6.0 mmol). The reaction mixture was stirred at −20° C. for 1 h, then poured into cold dilute HCl and extracted with CH$_2$Cl$_2$. The organic extract was washed with water, dilute aqueous NaHCO$_3$, brine, and dried (MgSO$_4$). Concentration in vacuo gave the desired compound as a colorless oil (2.20 g, 73%); $^1$H NMR (300 MHz, CDCl$_3$) δ 8.4 (m, 1H, NH), 5.12–4.90 (m, 2H), 4.38 (m, 1H), 4.11 (m, 1H), 4.00 (m, 1H), 2.73 (m, 1H), 2.42 (2m, 2H), 1.92 (m, 2H), 1.45 (s, 9H, t-Bu), 1.11–0.85 (m, 12H, 4×CH$_3$); $^{19}$F NMR δ −82.14 (s, CF$_3$), −120.99 and −123.09, −121.23 and −122.84 (2AB quartets, J=296 Hz, CF$_2$).

d) L-valyl-N-[3,3,4,4-pentafluoro-1-(1-methylethyl)-2-oxobutyl]-L-2-azetamide Hydrochloride Salt HCl gas was bubbled into a stirred solution of the product of part (c) (2.0 g, 3.98 mmol) in EtOAc (40 mL) at icebath temperature for 4 min. The reaction was then stirred at room temperature for 2 h, conc in vacuo and azeotroped with EtOAc to give the desired product (1.63 g, 96%) as a white foam; IR (film) 3196, 2972, 2937, 2883, 2636, 1755, 1655, 1523, 1471, 1398, 1373, 1350, 1222, 1201, 1159, 1116, 1093, 1066, 1014, 979, 922, 835, 815, 734, 646, 588; $^1$H NMR (300 MHz, CDCl$_3$) δ 8.09 (d, 1H, J=8.2 Hz, NH), 8.02 (d, 1H, J=8.5 Hz, NH), 5.15 (m, 1H), 5.00 (m, 1H), 4.55 (m, 1H), 4.13 (m, 1H), 3.90 (m, 1H), 2.56 (m, 2H), 2.30 (m, 3H), 1.12–0.84 (m, 12H, 4×CH$_3$); $^{13}$C NMR (CDCl$_3$) δ 193.2, 170.7, 170.4, 170.3, 169.9, 62.2, 61.5, 59.7, 59.5, 55.1, 55.0, 50.1, 30.0, 29.9, 28.9, 28.7, 19.8, 19.7, 18.8, 18.5, 18.2, 18.1, 17.8, 16.6, 16.3; $^{19}$F NMR δ −82.06 and −82.14 (2s, CF$_3$), −121.16 and −122.76, −121.33 and −122.88 (2AB quartets, J=296 Hz, CF$_2$); MS (Cl/CH$_4$) m/z (rel. intensity) 442 (6), 430 (18), 402 (MH+, 100), 303 (9), 72 (42). Anal. Cald. for C$_{16}$H$_{24}$F$_5$N$_3$O$_3$.HCl: C, 43.89; H, 5.53; N, 9.59. Found: C, 43.43; H, 6.07; N, 9.23.

e) N-[4-(4-morpholinylcarbonyl)benzoyl]-L-valyl-N'-[3,3,4,4,4-pentafluoro-1-(1-methylethyl)-2-oxobutyl]-L-2-azetamide (MDL 104,238)

To a stirred suspension of 4-(4-morpholinylcarbonyl) benzoic acid (975 mg, 4.14 mmol) and benzyltriethylammonium chloride (4 mg, 0.008 mmol) in 1,2-dicloroethane (30 mL) was added thionyl chloride (0.30 mL, 4.14 mmol) and the reaction was heated at reflux. After 2.5 h, the reaction was allowed to cool to room temperature and concentrated in vacuo. The residue was then azeotroped with CCl$_4$ and placed under vacuum to give morpholinoterephthalic acid chloride (quantitative) as a light orange oil which was used without further purification. In a separate RB flask, a stirred solution of the product of part (d) (1.5 g, 3.43 mmol) in CH$_2$Cl$_2$ (20 mL) was cooled to −20° C. NMM (1.35 mL, 12.3 mmol) was added and immediately followed by the dropwise addition of the morpholinoterephthalic acid chloride in CH$_2$Cl$_2$ (5 mL) at such a rate as to maintain the internal reaction temperature at −10° C. or less. After the addition was complete, the reaction mixture was allowed to warm to room temperature. After 1.5 h at room temperature, the reaction mixture was diluted with CH$_2$Cl$_2$ (20 mL), washed with 1N HCl (2×20 mL), saturated NaHCO$_3$ (2×20 mL), brine (1×20 mL), dried (MgSO$_4$) and conc. in vacuo to give a white foam which was immediately flash chromatographed (eluted with 1:27 MeOH—CH$_2$Cl$_2$) to give the desired product (MDL 104,238) (335 mg, 16%) as a white foam; IR (KBr) 3690, 3678, 3429, 3271, 3011, 2972, 2931, 2899, 2876, 2862, 1755, 1680, 1631, 1520, 1494, 1458, 1437, 1398, 1373, 1361, 1330, 1302, 1280, 1259, 1234, 1199, 1159, 1114, 1068, 1024, 1012, 896, 860, 842, 787, 773, 763, 669, 597, 563, 540; $^1$H NMR (300 MHz, CDCl$_3$) δ 8.32 (m, 1H, NH), 7.86 (d, 2H, J=8.5 Hz, aryl), 7.49 (d, 2H, J=7.9 Hz,aryl), 6.70 (m, 1H, NH), 5.00 (m, 2H), 4.50 (m, 2H), 4.19 (m, 1H), 4.86–3.30 (series of m, 8H), 2.82–1.95 (series of m, 4H), 1.05 (m, 9H, 3×CH$_3$), 0.88 (d, 3H, J=6.9 Hz, CH$_3$); $^{13}$C NMR δ 174.07, 174.05, 170.6, 169.2, 166.4, 138.66, 138.62, 135.0, 134.9, 127.4, 127.3, 66.8, 66.7, 62.0, 61.7, 59.7, 59.6, 54.1, 54.0, 49.3, 31.5, 31.4, 28.7, 28.5, 20.0, 19.0, 18.8, 18.2, 18.1, 18.09, 18.05, 16.1, 16.0; $^{19}$F NMR δ −82.12 (s, CF$_3$), −120.98 and −123.12, −121.20 and −122.86 (2AB quartets, J=296 Hz, CF$_2$); MS (Cl/CH$_4$) m/z (rel. intensity) 647, 619 (MH+), 303 (100), 289, 218. Anal. Calcd. for C$_{28}$H$_{35}$F$_5$N$_4$O$_6$.0.3H$_2$O: C, 53.90; H, 5.75; N, 8.98. Found: C, 53.75; H, 5.86; N, 8.86.

EXAMPLE 2

Preparation of N-[4-(4-morpholinylcarbonyl)benzoyl]-L-valyl-N'-[3,3,4,4,4-pentafluoro-1-(1-methylethyl)-2-oxobutyl]-D,L-2-pipecolinamide

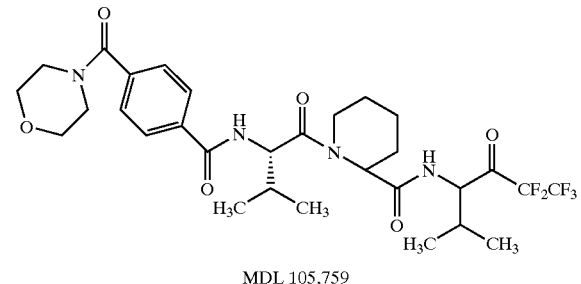

MDL 105,759 a) N-[(1,1-dimethylethoxy)carbonyl]-L-valyl-D,L-2-pipecolinic Acid

To a stirred solution of D,L-pipecolinic acid (1.30 g, 10 mmol) and Et$_3$N (1.5 mL, 11 mmol) in DMF (30 mL) was added the product of example 1, part (a) (2.0 g, 6.0 nmmol) and the reaction was heated to 120° C. for 2.5 h. Upon cooling, the reaction was conc in vacuo and the oily residue was dissolved in EtOAc and washed with 3 N HCl (2×30 mL), dried (Na$_2$SO$_4$) and conc to a yellow foam which was flash chromatographed to give the desired compound (579 mg, 29%), a mixture of two compounds, as a white foam; $^1$H NMR (300 MHz, CDCl$_3$) δ 8.94 (br s, 1H), 5.62 (d, 1H, J=9.8 Hz, NH), 5.45 (d, 0.5H, J=3.98 Hz, L-Pec), 5.07 (d, 0.5H, J=9.25, D-Pec), 4.60 (dd, 0.5H, J=8.83, 5.06 Hz, α-CH of Val), 4.25 (dd, 0.5H, J=8.69, 4.66 Hz, Val of D-compound), 3.93 (app d, 1H, J=12.47 Hz, Pec), 3.25 (m, 1H, Pec), 2.31 (m, 1H, Pec), 2.20 (m, 0.5H, Val of D-compound), 2.01 (m, 0.5H, Val), 1.78–1.33 (m, 5H, Pec), 1.44 (s, 9H, tBu), 1.01–0.86 (m, 6H, 2×CH$_3$).

b) N-[1,1-dimethylethoxy)carbonyl]-L-valyl-N'-[3,3,4,4,4-pentafluoro-1-(1-methylethyl)-2-oxobutyl]-D,L-2-pipecolinamide To a stirred solution of the product of example 2, part (a) (450 mg, 1.37 mmol) and NMM (0.15 mL, 1.37 mmol) in dry $CH_2Cl_2$ (20 mL) at −20° C. under nitrogen was added dropwise isobutylchloroformate (0.18 mL, 1.37 mmol). After 20 min, 4-amino-1,1,1,2,2-pentafluoro-5-methyl-3-hexanone hydrochloride (351 mg, 1.37 mmol). The reaction mixture was stirred at −20° C. for 1 h, then poured into cold dilute HCl and extracted with $CH_2Cl_2$. The organic extract was washed with water, dilute aqueous $NaHCO_3$, brine, and dried ($MgSO_4$). Concentration in vacuo gave the desired compound (580 mg, 80%) as a colorless foam; $^1H$ NMR (300 MHz, $CDCl_3$) δ 6.98 (m, 1H, NH), 5.36–4.88 (m, 3H), 4.60 (m, 1H), 4.43 (m, 1H), 3.92 (m, 1H), 3.10 (m, 1H, CH of Pec), 2.36–1.92 (series of m, 3H, Pec and CH or Val), 1.79–1.24 (m, 4H), 1.45 (s, 9H, tBu), 1.05–0.83 (m, 12H, 4×$CH_3$); $^{19}F$ NMR δ −82.10 (s, $CF_3$), −120.74—−123.40 (m, $CF_2$).

c) N—L-valyl-N'-[3,3,4,4,4-pentafluoro-1-(1-methylethyl)-2-oxobutyl]-D,L-2-pipecolinamide, Hydrochloride Salt HCl gas was bubbled into a stirred solution of the product of example 2 (b) (530 mg, 1.0 mmol) in EtOAc (10 mL) at icebath temperature for 4 min. The reaction was then stirred at room temperature for 2 h, conc in vacuo and azeotroped with EtOAc to give the desired compound (460 mg, 99%) as a white foam.

d) N-[4-(4-morpholinylcarbonyl)benzoyl]-L-valyl-N'-[3,3,4,4,4-pentafluoro-1-(1-methylethyl)-2-oxobutyl]-D,L-2-pipecolinamide (MDL 105,759)

To a stirred suspension of 4-(4-morpholinylcarbonyl)benzoic acid (0.28 g, 120 mmol) and benzyltriethylammonium chloride (2 mg, 0.004 mmol) in 1,2-dichloroethane (25 mL) was added thionyl chloride (0.09 mL, 1.20 mmol) and the reaction was heated to reflux. After 2.5 h, the reaction was allowed to cool to room temperature and concentrated in vacuo. The residue was then azeotroped with $CCl_4$ and placed under vacuum to give morpholinoterephthalic acid chloride (quantitative) as a light orange oil which was used without further purification. In a separate RB flask, a stirred solution of the product of example 2 (c) (450 mg, 10.0 mmol) in $CH_2Cl_2$ (10 mL) was cooled to −20° C. NMM (0.5 mL, 4.0 mmol) was added and immediately followed by the dropwise addition of the morpholinoterephthalic acid chloride in $CH_2Cl_2$ (5 mL) at such a rate as to maintain the internal reaction temperature at −10° C. or less. After the addition was complete, the reaction mixture was allowed to warm to room termperature. After 1.5 h at room temperature, the reaction mixture was diluted wiith $CH_2Cl_2$ (20 mL), washed with 1N HCl (2×20 mL), saturated $NaHCO_3$ (2×20 mL), brine (1×20 mL), dried ($MgSO_4$) and conc in vacuo to give a crude foam (410 mg). The crude white foam was immediately flash chromatographed (eluted with 1:27 MeOH—$CH_2Cl_2$) to give the desired product (MDL 105,759)(270 mg, 42%) as a white foam;

$^1H$ NMR (300 MHz, $CDCl_3$) δ 7.95–7.76 (m, 2H, aryl), 7.58–7.39 (m, 2H), 7.20–6.86 (m, 2H, aryl), 5.40–4.30 (m, 4H), 4.20–3.20 (m, 10H, 2×$NCH_2CH_2O$ and $NCH_2$ of Pro), 2.60–1.95 (m, 3H), 1.90–1.82 (m, 4H), 1.25–0.75 (m, 12H); $^{19}F$ NMR ($CDCl_3$) δ −81.97 (m, $CF_3$), −121.82 and −119.87 (m, $CF_2$); MS (Cl/$CH_4$) m/z (rel. intensity) 647 (MH+), 564, 536, 474, 428, 363, 331 (100), 317, 289, 246, 218, 186, 158, 104, 84, 72.

EXAMPLE 3
Preparation of N-[4-(4-morpholinylcarbonyl)benzoyl]-L-valyl-N'-[3,3,4,4,4-pentafluoro-1-(1-methylethyl)-2-oxobutyl]-trans-4-hydroxyprolinamide

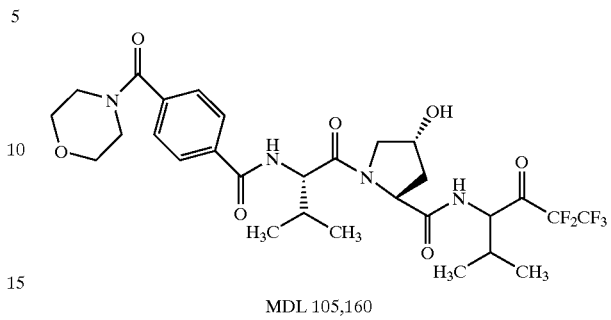

MDL 105,160 a) N-[(1,1-dimethylethoxy)carbonyl]-L-valyl-trans-4-hydroxyproline

To a stirred solution of trans-4-hydroxy-L-proline (1.31 g, 10 mmol) and $Et_3N$ (1.4 mL, 10 mmol) in DMF (40 mL) was added the product of example 1 (a) (3.14 g, 10 mmol) and the reaction was heated to 110° C. for 3 h. Upon cooling, the reaction was conc in vacuo and the oily residue was dissolved in EtOAc and washed with 3N HCl (2×30 mL), $H_2O$ (2×10 mL), dried ($Na_2SO_4$) and conc. to give the desired compound (1.85 g, 56%) as a white foam; $^1H$ NMR (300 MHz, $CDCl_3$) δ 5.70–5.25 (m, 1H, NH), 5.05 (m, 1H), 4.80–3.95 (m, 4H), 3.85–2.80 (series of m, 3H), 2.35–1.80 (m, 2H), 1.44 (s, 9H, tBu), 1.01–0.95 (m, 6H, 2×$CH_3$); MS(CI/$CH_4$) m/Z (rel intensity), 331(MH+), 303, 275 (100), 259, 231, 217, 172, 162, 144, 132, 116, 86, 72.

b) N-[(1,1-dimethylethoxy)carbonyl]-L-valyl-N'-[3,3,4,4,4-pentafluoro-1-(1-methylethyl)-2-oxobutyl]-trans-4-hydroxyprolinamide To a stirred solution of the product of example 3 (a) (1.80 g, 5.60 mmol) and NMM (0.60 mL, 5.60 mmol) in dry $CH_2Cl_2$ (30 mL) at −20° C. under nitrogen was added dropwise isobutylchloroformate (0.70 mL, 5.60 mmol). After 20 min, 4-amino-1,1,1,2,2-pentafluoro-5-methyl-3-hexanone hydrochloride (1.40 g, 5.60 mmol) was added, immediately followed by another equivalent of NMM (0.60 mL, 5.60 mmol). The reaction mixture was stirred at −20° C. for 1 h, then allowed to warm to room temperature and poured into cold, dilute HCl and extracted with $CH_2Cl_2$. The organic extract was washed with water, dilute aqueous $NaHCO_3$, brine, dried ($MgSO_4$) and conc in vacuo to give a crude oil which was flash chromatographed (5% MeOH/$CH_2Cl_2$) to give the desired compound (1.44 g, 48%) as a white foam; $^1H$ NMR (300 MHz, $CDCl_3$) δ 7.98 (br d, 0.5H, J=7.6 Hz, NH), 7.73 (br d, 0.5H, J=7.6 Hz, NH), 5.47 (br d, 1H, J=8.6 Hz, NH), 5.04–4.95 (m, 1H), 4.76–4.67 (m, 1H), 4.49 (br s, 1H), 4.23 (m, 1H), 3.94 (br d, 1H, J=10.8 Hz), 3.66–3.59 (m, 1H), 2.50–1.98 (series of m, 4H), 1.42 (s, 9H, t-Bu), 1.09–0.88 (m, 12H, 4×$CH_3$); $^{13}C$ NMR δ 173.9, 173.2, 170.6, 170.4, 156.3, 156.2, 80.5, 80.4, 77.4, 77.2, 77.0, 76.5, 70.0, 69.8, 59.7, 59.5, 58.2, 57.7, 57.6, 55.7, 55.5, 35.7, 34.7, 31.0, 30.9, 29.0, 28.6, 28.3, 28.2, 20.2, 19.9, 19.3, 19.7, 18.3, 18.2, 16.4, 16.1; $^{19}F$ NMR δ −82.17 (s, $CF_3$), −82.18 (s, $CF_3$), −121.6 and −122.8 (AB quartet, J=296 Hz, $CF_2$); MS(CI/$CH_4$) m/z (rel intensity) 549 ($MNH_4$+, 12), 532 (MH+, 54), 482 (11), 330 (15), 245 (100), 189 (15).

c) N—L-valyl-N'-[3,3,4,4,4-pentafluoro-1-(1-methylethyl)-2-oxobutyl]-trans-4-hydroxyprolinamide, Hydrochloride Salt and N—L-valyl-N'-[3,3,4,4,4-pentafluoro-1-(1-methylethyl)-2-oxobutyl]-trans-4-acetoxyprolinamide, Hydrochloride Salt HCl gas was bubbled into a stirred solution of the product of example 3 (b) (1.44 g, 2.70 mmol) in EtOAc (20 mL) at icebath temperature for 4 min. The reaction was then stirred at room temperature for 2 h, conc in vacuo and azeotroped with EtOAc to give the desired combination of derivatives (1.27 g, 100%), the acetoxy derivative being the minor derivative, as a white foam.

d) N-[4-(4-morpholinylcarbonyl)benzovl]-L-valyl-N'-[3,3,4,4,4-pentafluoro-1-(1-methylethyl)-2-oxobutyl]-trans-4-hydroxyprolinamide (MDL 105,160) and N-L-valyl-N'-[3,3,4,4,4-pentafluoro-1-(1-methylethyl)-2-oxobutyl]-trans-4-acetoxyprolinamide (MDL 105,683)

To a stirred suspension of 4-(4-morpholinylcarbonyl) benzoic acid (280 mg, 1.90 mmol) and benzyltriethylammonium chloride (2 mg, 0.004 mmol) in 1,2-dichloroethane (20 mL) was added thionyl chloride (0.15 mL, 1.90 mmol) and the reaction was heated at reflux. After 2 h, the reaction was allowed to cool to room temperature and concentrated in vacuo. The residue was then azeotroped with $CCl_4$ and placed under vacuum to give morpholinoterephthalic acid chloride (quantitative) as a light orange oil which was used without further purification. In a separate RB flask, a stirred solution of the product of example 3 (c) (800 mg, 1.71 mmol) in $CH_2Cl_2$ (15 mL) was cooled to -20° C. NMM (0.42 mL, 3.80 mmol) was added and immediately followed by the dropwise addition of the morpholinoterephthalic acid chloride in $CH_2Cl_2$ (5 mL) at such a rate as to maintain the internal reaction temperature at -10° C. or less. After the addition was complete, the reaction mixture was allowed to warm to room termperature. After 2 h at room temperature, the reaction mixture was diluted with $CH_2Cl_2$ (20 mL), washed with 1N HCl (2×20 mL), saturated $NaHCO_3$ (2×20 mL), brine (1×20 mL), dried ($Na_2SO_4$) and conc in vacuo to give a mixture of two compounds (MDL 105,160 as the major product and MDL 105,683 as the minor product) as a crude foam.

e) N-[4-(4-morpholinylcarbonyl)benzoyl]-L-valyl-N'-[3,3,4,4,4-pentafluoro-1-(1-methylethyl)-2-oxobutyl]-trans-4-hydroxyprolinamide (MDL 105,160)

The mixture of the two compounds defined in example 3(d) was immediately flash chromatographed on $SiO_2$, eluting with 1:27 MeOH—$CH_2Cl_2$ to yield the desired compound (MDL 105,160) (160 mg, 14.5%) as the higher $R_f$ material ($R_f$ of about 0.3–0.4) as a white foam; $^1$H NMR (300 MHz, $CDCl_3$) δ 7.82 (m, 2H, aryl), 7.45 (d, 2H, J=8.3 Hz, aryl), 7.35 (d, 0.5H, J=8.4 Hz, NH), 6.91 (d, 1H, J=8.7 Hz, NH), 4.99 (m, 1H), 4.84 (t, 1H), 4.72 (t, 1H), 4.68 (m, 1H), 4.55 (br s, 1H), 4.18 (m, 1H), 3.8–3.4 (br s overlapping m, 9H), 2.86–2.03 (series of m, 4H), 1.26 (m, 9H, 3×$CH_3$), 0.96 (m, 3H, $CH_3$); $^{13}$C NMR δ 173.2, 172.5, 170.7, 170.4, 169.2, 167.1, 138.8, 134.9, 127.52, 127.50, 127.4, 127.3, 77.55, 77.52, 77.51, 77.46, 77.44, 77.3, 77.2, 77.1, 77.0, 76.88, 76.85, 76.6, 76.56, 76.54, 70.1, 69.9, 66.8, 59.6, 59.5, 58.5, 57.9, 57.0, 56.0, 56.0, 55.7, 36.0, 34.9, 31.42, 31.40, 31.3, 29.2, 28.8, 20.0, 19.85, 19.83, 19.4, 19.2, 18.4, 16.5, 16.4, 16.3, 16.2; $^{19}$F NMR ($CDCl_3$) δ -82.1, -82.15 (s, $CF_3$), -121.31, -123.02 (AB quartet J=293 Hz, $CF_2$) and -121.35, -122.82 (AB quartet, J=298 Hz, $CF_2$); MS (Cl/$CH_4$) m/z (rel intensity) 649 (MH$^+$), 361, 334, 333 (100), 317, 289, 218, 200, 111, 86. Anal. Calcd. for $C_{29}H_{37}F_5N_4O_7$: C, 53.70; H, 5.75; N, 8.64. Found: C, 53.44; H, 5.77; N, 8.38.

EXAMPLE 4

Preparation of N-[4-(4-morpholinylcarbonyl)benzoyl]-L-valyl-N'-[3,3,4,4,4-pentafluoro-1-(1-methylethyl)-2-oxobutyl]-trans-4-acetoxyprolinamide

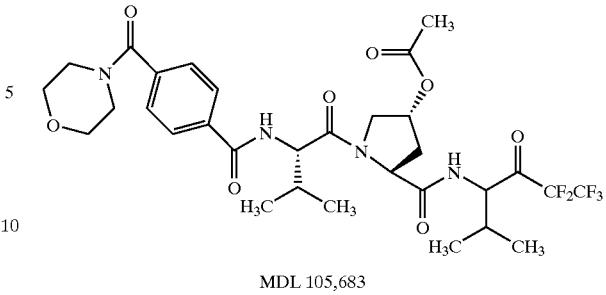

MDL 105,683 a) N—L-valyl-N'-[3,3,4,4,4-pentafluoro-1-(1-methylethyl)-2-oxobutyl]-trans-4-acetoxyprolinamide (MDL 105,683)

MDL 105,683 was obtained as the lower $R_f$ material ($R_f$ of about 0.05–0.1) from the mixture of the two compounds which was flash chromatographed as described in example 3(e). Said process yielded MDL 105,683 (90 mg, 7.6%) as a white foam; $^1$H NMR (300 MHz, $CDCl_3$) δ 7.84 (d, 2H, J=8.4 Hz, aryl), 7.72 (0.5H, J=8.4 Hz, NH), 7.47 (d, 2H, J=8.3 Hz, aryl), 6.74 (d, 1H, J=8.6 Hz, NH), 5.36 (m, 1H), 5.00 (m, 1H), 4.83 (dd, 0.5H, J=8.6, 7.2 Hz), 4.69 (t, 0.5H), 4.08 (br d, 1H), 3.9–3.3 (br s overlapping m, 9H), 2.81 (m, 0.5H), 2.64 (m, 0.5H), 2.41–2.06 (series of m, 3H), 2.04 (s, 3H, $OCH_3$), 1.02 (m, 9H, 3×$CH_3$), 0.94 (m, 3H, $CH_3$); $^{13}$C NMR δ 173.0, 172.3, 170.4, 170.1, 169.9, 169.2, 166.3, 138.7, 127.4, 127.3, 72.5, 72.4, 66.8, 59.6, 59.5, 58.5, 57.8, 56.3, 56.2, 53.2, 52.9, 34.0, 32.8, 31.8, 31.7; 31.6, 29.3, 29.2, 28.8, 24.9, 20.9, 20.0, 19.8, 19.5, 19.3, 17.95, 17.92, 17.7, 16.4, 16.2; $^{19}$F NMR ($CDCl_3$) δ -82.1, -82.13 (s, $CF_3$), -121.22, -123.06 (AB quartet J=296 Hz, $CF_2$) and -121.28, -122.86 (AB quartet, J=301 Hz, $CF_2$); MS(Cl/$CH_4$) m/z (rel intensity) 691 (MH+), 631, 472, 444, 389, 375 (100), 349, 318, 317, 289, 264, 225, 218, 128, 100. Anal. Calcd. for $C_{31}H_{39}F_5N_4O_8$: C, 53.91; H, 5.69; N, 8.11. Found: C, 54.40; H, 5.79; N, 8.15.

EXAMPLE 5

Preparation of N-[4-(4-morpholinylcarbonyl)benzoyl]-L-valyl-N'-[3,3,4,4,4-pentafluoro-1-(1-methylethyl)-2-oxobutyl]-trans-4-benzyloxyprolinamide

MDL 104,865 a) trans-4-benzyloxyproline, Hydrochloride Salt

HCl (g) was bubbled for 2 min into an ice cooled solution of t-butyloxycarbonyl-O-benzyl-L-hydroxyproline (5.0 g, 15.6 mmol) in EtOAc (30 mL). The reaction was then stoppered, stirred at room temperature for 1 h and conc in vacuo to provide a white solid which was triturated with ether and dried under vacuum to yield the desired compound (3.92 g, 98%), mp 188–190° C.; $^1$H NMR (300 MHz, $CDCl_3$) δ 9.1 (br s, 1H), 7.3 (m, 5H), 4.56 (s, 2H), 4.4–4.2 (m, 2H), 3.6–3.38 (m, 3H), 2.6–2.58 (m, 1H), 2.26–2.1 (m, 1H); m/z (rel. intensity) 262 (M++C$_3$H$_5$), 250 (M++C$_2$H$_5$), 222 (MH+, 100), 176, 130, 107, 91, 85, 69.

b) N-[(1,1-dimethylethoxy)carbonyl]-L-valyl-trans-4-benzyloxyproline

To a stirred solution of trans-4-benzyloxy-L-proline, hydrochloride salt (2.57 g, 10 mmol) and Et$_3$N (3.0 mL, 22 mmol) in DMF (25 mL) was added the product of example 1 (a) (3.14 g, 10 mmol) and the reaction was heated to 80° C. for 1.5 h. Upon cooling, the reaction was conc in vacuo and the oily residue was dissolved in EtOAc and washed with 3N HCl (2×30 mL), H$_2$O (2×10 mL), dried (Na$_2$SO$_4$) and conc. to give the desired compound (1.8 g, 42%). Crystallization (EtOAc/hexane) afforded a white solid: mp 125–128° C.; $^1$H NMR (300 MHz, CDCl$_3$) δ 8.0 (br s, 1H), 7.4–7.2 (m, 5H), 5.35 (d, 1H, J=9.2 Hz, NH), 4.65 (m, 1H), 4.52 (m, 2H), 3.70 (m, 1H), 2.5–1.8 (series of m, 3H), 1.44 (s, 9H, tBu), 0.98 (d, 3H, J=6.8 Hz, CH$_3$), 0.92 (d, 3H, J=6.8 Hz, CH$_3$).

c) N-[(1,1-dimethylethoxy)carbonyl]-L-valyl-N'-[3,3,4,4,4-pentafluoro-1-(1-methylethyl)-2-oxobutyl]-trans-4-benzyloxyprolinamide To a stirred solution of the product of example 5 (b) (1.40 g, 3.30 mmol) and NMM (0.36 mL, 3.30 mmol) in dry CH$_2$Cl$_2$ (20 mL) at −20° C. under nitrogen was added dropwise isobutylchloroformate (0.43 mL, 3.30 mmol). After 20 min, 4-amino-1,1,1,2,2-pentafluoro-5-methyl-3-hexanone hydrochloride (840 mg, 3.30 mmol) was added, immediately followed by another equivalent of NMM (0.36 mL, 3.30 mmol). The reaction mixture was stirred at −20° C. for 1 h, then allowed to warm to room temperature and poured into cold, dilute HCl and extracted with CH$_2$Cl$_2$. The organic extract was washed with water, dilute aqueous NaHCO$_3$, brine and dried (Na$_2$SO$_4$) and conc in vacuo to yield the desired compound (2.0 g, 95%) as a white solid: mp 91–93° C.; $^1$H NMR (300 MHz, CDCl$_3$) δ 7.96 (0.5H, NH), 7.33 (m, 5H), 5.28 (m, 1H, NH), 4.95 (m, 1H), 4.83 (m, 1H), 4.70 (t, 0.5H), 4.54 (q, 2H, CH$_2$Ph), 4.30 (m, 2H), 4.07–3.9 (m, 1H), 3.60 (m, 1H), 2.68 (dt, 0.5H), 2.49 (dt, 0.5H), 2.33 (m, 1H), 2.2–1.88 (m, 1H), 1.44 (s, 9H, tBu), 1.09–0.86 (m, 12H, 4×CH$_3$).

d) N—L-valyl-N'-[3,3,4,4,4-pentafluoro-1-(1-methylethyl)-2-oxobutyl]-trans-4-benzyloxyprolinamide, Hydrochloride Salt HCl gas was bubbled into a stirred solution of the product of example 5 (c) (330 mg, 0.53 mmol) in EtOAc (10 mL) at icebath temperature for 2 min. The reaction was then stirred at room temperature for 1 h, conc in vacuo and azeotroped with EtOAc to give the desired compound (240 mg, 81%) as a white foam; $^1$H NMR (300 MHz, CDCl$_3$) δ 8.22 (m, 2H, NH$_2$), 7.33 (m, 5H), 5.04 (app q, 1H), 4.88 (dq, 1H), 4.52 (q, 2H, CH$_2$Ph), 4.33 (m, 1H), 4.0–3.8 (series of m, 4H), 2.42–2.1 (m, 4H), 1.09–0.86 (m, 12H, 4×CH$_3$).

e) N-[4-(4-morpholinylcarbonyl)benzoyl]-L-valyl-N'-[3,3,4,4,4-pentafluoro-1-(1-methylethyl)-2-oxobutyl]-trans-4-benzyloxyprolinamide (MDL 104,865)

To a stirred suspension of 4-(4-morpholinylcarbonyl) benzoic acid (280 mg, 1.90 mmol) and benzyltriethylammonium chloride (2 mg, 0.004 mmol) in 1,2-dichloroethane (20 mL) was added thionyl chloride (0.15 mL, 1.90 mmol) and the reaction was heated at reflux. After 2 h, the reaction was allowed to cool to room temperature and concentrated in vacuo. The residue was then azeotroped with CCl$_4$ and placed under vacuum to give morpholinoterephthalic acid chloride (quantitative) as a light orange oil which was used without further purification. In a separate RB flask, a stirred solution of the product of example 5 (d) (558 mg, 1.0 mmol) in CH$_2$Cl$_2$ (15 mL) was cooled to −20° C. NMM (0.40 mL, 4.0 mmol) was added and immediately followed by the dropwise addition of the morpholinoterephthalic acid chloride in CH$_2$Cl$_2$ (5 mL) at such a rate as to maintain the internal reaction temperature at −10° C. or less. After the addition was complete, the reaction mixture was allowed to warm to room termperature. After 2 h at room temperature, the reaction mixture was diluted wiith CH$_2$Cl$_2$ (20 mL), washed with 1N HCl (2×20 mL), saturated Na$_2$HCO$_3$ (2×20 mL), brine (1×20 mL), dried (Na$_2$SO$_4$) and conc in vacuo to give a crude foam which was immediately flash chromatographed (eluted with 1:27 MeOH—CH$_2$Cl$_2$) to give the desired product (520 mg, 70%) as a white foam; $^1$H NMR (300 MHz, CDCl$_3$) δ 7.84 (dd, 2H, aryl), 7.78 (d, 0.5H, NH), 7.45 (dd, 2H, aryl), 7.29 (m, 5H), 7.21 (d, 0.5H, NH), 6.87 (d, 1H, NH), 4.98 (m, 1H), 4.82 (m, 1H), 4.69 (t, 0.5H), 4.54 (dq, 2H, CH$_2$Ph), 4.31 (br s, 1H), 4.08 (dq, 1H), 3.9–3.25 (series of m, 9H), 2.69 (dt, 0.5H), 2.46 (dt, 0.5H), 2.34 (m, 1H), 2.17 (m, 1H), 1.02 (m, 9H, 3×CH$_3$), 0.89 (m, 3H, CH$_3$);
$^{13}$C NMR (CDCl$_3$) δ 193.1, 172.9, 172.2, 170.7, 170.4, 169.3, 166.2, 138.4, 137.5, 137.4, 135.2, 128.5, 128.4, 128.2, 127.9, 127.8, 127.78, 127.73, 127.71, 127.5, 127.4, 127.3, 119.5, 115.76, 107.1, 106.6, 71.4, 71.2, 66.7, 59.6, 59.4, 58.7, 58.0, 56.0, 52.6, 52.3, 48.14, 48.11, 48.10, 48.0, 42.6, 42.57, 42.52, 42.4, 33.5, 32.4, 31.8, 29.1, 28.6, 20.0, 19.8, 19.4, 19.3, 17.8, 17.6, 16.3, 16.1; $^{19}$F NMR (CDCl$_3$) δ−82.10, −82.13 (s, CF$_3$), −121.3, −122.9 and −121.4, −122.8 (AB quartet, J=296 Hz, CF$_2$); MS(CI/CH$_4$) m/z (rel. intensity) 767 (M++29), 740 (10), 739 (MH+, 27), 632 (11), 520 (7), 492 (5), 424 (18), 423 (100), 403 (3), 345 (5), 317 (30), 289 (4), 218 (3), 176 (11), 91 (2).

Anal. Calcd. for C$_{36}$H$_{43}$F$_5$N$_4$O$_7$·0.4H$_2$O: C, 57.95; H, 5.92; N, 7.54. Found: C, 58.10; H, 5.84; N, 7.49.

EXAMPLE 6

Alternative Preparation of Boc-Val-CF$_2$CF$_3$

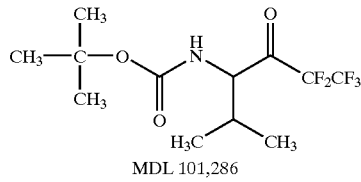

MDL 101,286

A mixture of 288.0 g (1.11 mol) of Boc-Val N-methyl-O-methyl hydroxamic acid and 4.7L of anhydrous Et$_2$O was charged to a 12-L 3-necked flask fitted with a stirrer, thermometer, dry ice condenser, gas dispersion tube and continuous N$_2$ purge. The resulting solution was cooled to −60° C. to −65° C. A total of 885.2 g (3.60 mol) of C$_2$FSI was added via a gas dispersion tube over about 30 min to the solution of Boc-Val N-methyl-O-methyl hydroxamic acid while maintaining a temperature of about −65° C. Immediately upon completing the gas addition, a total of 2.39L of 1.5M CH$_3$Li·LiBr in Et$_2$O (3.59 mol) was added over 1 h maintaining a reaction temperature of −52° C. to −58° C. A precipitate formed after about ⅓ of the CH$_3$Li·LiBr had been added but a complete solution was present at the end of the addition. The resulting solution was stirred at −52° C. to −58° C. for 1 h. The reaction was monitored by GC (Rt of MDL 101,286=1.3 min, Rt of Boc-Val N-methyl-O-methyl hydroxamic acid=5.1 min) and found to contain 7.2% of Boc-Val N-methyl-O-methyl hydroxamic acid. A total of 255 mL (3.47 mol) of acetone was added over about 15 min maintaining a reaction temperature of −52° C. to −58° C. and the resulting mixture was stirred for 10 min. The mixture was quenched into a 22L flask containing 4.7L of 0.75M KHSO$_4$ which had been cooled to about 0° C. The organic layer was separated and washed with 3L of H$_2$O. The organic layer was dried using 500 g of MgSO$_4$ and filtered to remove the drying agent. The filtrate was concentrated at 40° C./100 torr to a semi-solid weighing 409 g. The crude material was dissolved in 1.2L of hexane at 45° C. and cooled slowly over about 30 min to −25° C. to −30° C. The solid which crystallized was filtered off and washed with 250 mL of hexane at −30° C. The MDL 101,286 obtained was vacuum dried (25° C./100 torr) to give 176.7 g. The filtrate was concentrated at 35° C./100 torr to a residue weighing 153.5 g. The material was put on a Kugelrohr distillation apparatus and a forerun was collected up to 40° C./0.6 torr. The receiver was changed and a total of 100.5 g of crude MDL 101,286 was collected at 40° C.–60° C./0.6 torr. The crude product was dissolved in 500 mL of hexane at about 50° C. The resulting solution was cooled to −30° C. The solid which crystallized was filtered off and washed with 100 mL of cold (−30° C.) hexane. The product was vacuum dried at 25° C./100 torr to give another 68.0 g of MDL 101,286 for a total yield of 244.7 g (70% yield) which was 99.9% pure by GC.

Anal. Calcd. for $C_{12}H_{18}F_5NO_3$ (319.28): C, 45.14, H, 5.68, N, 4.39; Found: C, 45.30, 45.49, H, 5.50, 5.58, N, 4.26, 4.35.

In a further embodiment, the present invention provides a method for the treatment of a patient afflicted with a neutrophil associated inflammatory disease comprising the administration thereto of a therapeutically effective amount of a compound of formula I. The term "neutrophil associated inflammatory disease" refers to diseases or conditions characterized by the migration of neutrophils to the site of inflamation and its participation in proteolytic degradation of biological matirces. Neutrophil associated inflammatory diseases for which treatment with a compound of formula I will be particularly useful include: emphysema, cystic fibrosis, adult respiratory distress syndrome, septicemia, disseminated intravascular coagulation, gout, rheumatoid arthritis, chronic bronchitis and inflammatory bowel disease. Compounds of formula I which are particularly preferred for the treatment of neutrophil associated inflammatory diseases include:

N-[4-(4-morpholinylcarbonyl)benzoyl]-L-valyl-N'-[3,3,4,4, 4-pentafluoro-1-(1-methylethyl)-2-oxobutyl]-L-2-azetamide;

N-[4-(4-morpholinylcarbonyl)benzoyl]-L-valyl-N'-[3,3,4,4, 4-pentafluoro-1-(1-methylethyl)-2-oxobutyl]-D,L-2-pipecolinamide;

N-[4-(4-morpholinylcarbonyl)benzoyl]-L-valyl-N'-[3,3,4,4, 4-pentafluoro-1-(1-methylethyl)-2-oxobutyl]-trans-4-hydroxyprolinamide;

N-[(4-(4-morpholinylcarbonyl)benzoyl]-L-valyl-N'-[3,3,4, 4,4-pentafluoro-1-(1-methylethyl)-2-oxobutyl]-trans-4-acetoxyprolinamide;

N-[4-(4-morpholinylcarbonyl)benzoyl]-L-valyl-N'-[3,3,4,4, 4-pentafluoro-1-(1-methylethyl)-2-oxobutyl]-trans-4-benzyloxyprolinamide.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

The term "therapeutically effective amount" refers to an amount which is effective, upon single or multiple dose administration to the patient, in providing relief of symptoms associated with neutrophil associated inflammatory diseases. As used herein, "relief of symptoms" of a respiratory disease refers to a decrease in severity over that expected in the absence of treatment and does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula I is expected to vary from about 0.1 milligram per kilogram of body weight per day (mg/kg/day) to about 100 mg/kg/day. Preferred amounts are expected to vary from about 0.5 to about 10 mg/kg/day.

The compounds of this invention are highly potent inhibitors of elastase, particularly human neutrophil elastase. It is believed that the compounds of this invention exert their inhibitory effect through inhibition of the enzyme elastase and thereby provide relief for elastase-mediated diseases including but not limited to emphysema, cystic fibrosis, adult rspiratory distress syndrome, septicemia, disseminated intravascular coagulation, gout and rheumatoid arthritis. However, it is understood that the present invention is not limited by any particular theory or proposed mechanism to explain its effectiveness in an end-use application.

In effecting treatment of a patient afflicted with a disease state described above, a compound of formula I can be administered in any form or mode which makes the compound bioavailable in effective amounts, including oral, aerosol, and parenteral routes. For example, compounds of formula I can be administered orally, by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formula I in admixture or otherwise in association with one or more inert carriers. These compositions are useful, for example, as assay standards, as convenient means of making bulk shipments, or as pharmaceutical compositions. An assayable amount of a compound of formula I is an amount which is readily measurable by standard assay procedures and techniques as are well known and appreciated by those skilled in the art. Assayable amounts of a compound of formula I will generally vary from about 0.001% to about 75% of the composition by weight. Inert carriers can be any material which does not degrade or otherwise covalently react with a compound of formula I. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula I in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula I of the present invention may also be administered by aerosol. The term aerosol is used to denote a variety of systems ranging from those of colloidal nature to systems consisting of pressurized packages. Delivery may be by a liquified or compressed gas or by a suitable pump system which dispenses the active ingredients. Aerosols of compounds of formula I may be delivered in single phase, bi-phasic, or tri-phasic systems in order to deliver the active ingredient. Delivery of the aerosol includes the necessary container, activators, valves, subcontainers, and the like. Preferred aerosol are able to be determined by one skilled in the art.

The compounds of formula I of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula I or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Human neutrophil elastase is assayed in vitro using N-MeOSuc-Ala-Ala-Pro-Val-p-nitroanilide, available commercially, as substrate. The assay buffer, pH and assay techniques are similar to those described by Mehdi, et al., *Biochemical and Biophysical Research Communications,* 166, 595 (1990). Enzyme is purified from human sputum, although recently it has become commercially available. Kinetic characterization of immediate inhibitors is by means of the Dixon plot, whereas the characterization of slow- and/or tight-binding inhibitors used data analysis techniques reviewed by Williams and Morrison. The synthesis and analytical use of a highly sensitive and convenient substrate of elastase is described in J. Bieth, B. Spiess and C. G. Wermuth, *Biochemical Medicine,* 11 (1974)350–375. Table 2 summarizes the ability of selected compounds of this invention to inhibit elastase.

TABLE 2

| MDL # | P₂ | $K_i$ (nM)* |
|---|---|---|
| 104,238 | azetidine | 34 |
| 105,759 | piperidine | 150 |
| 105,160 | 4-hydroxy pyrrolidine | 120 |

TABLE 2-continued

| MDL # | P₂ | $K_i$ (nM)* |
|---|---|---|
| 105,683 | 4-acetoxy pyrrolidine | 40 |
| 104,865 | 4-benzyloxy pyrrolidine | 20 |

*for human neutrophil elastase, using N-MeOSucAlaAlaProVal-pNA as substrate

---

What is claimed is:

1. A compound of the formula:

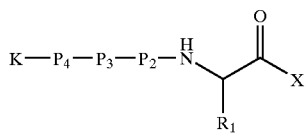

(I)

or a hydrate or a pharmaceutically acceptable salt thereof, wherein $P_4$ is Ala, bAla, Leu, Ile, Val, Nva, bVal, Nle or a bond;

$P_3$ is Ala, bAla, Leu, Ile, Val, Nva, bVal, Nle, or Lys substituted on its epsilon amino group with a morpholino-B-group;

$P_2$ is Pro(4-OBzl);

$R_1$ is a side chain of Ala, Leu, Ile, Val, Nva or bVal;

X is $CF_2CF_3$

K is

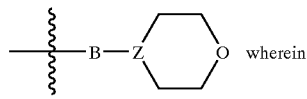 wherein

Z is N or CH, and

B is a group of the formula:

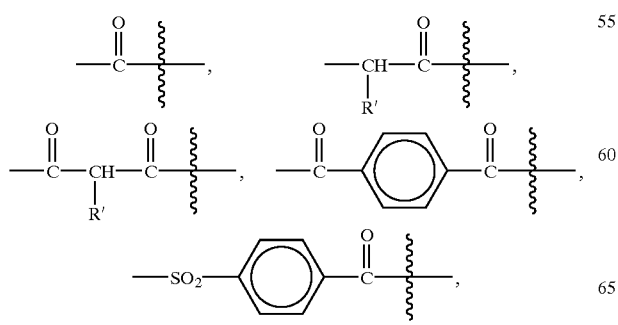

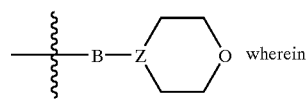

and wherein R' is hydrogen or a $C_{1-6}$alkyl group.

2. The compound of claim 1 wherein $R_1$ is —$CH(CH_3)_2$ or —$CH_2CH_2CH_3$.

3. The compound of claim 1 wherein K is

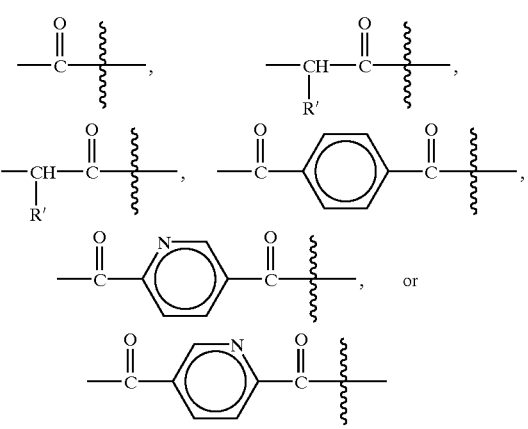

wherein

Z is N and

B is a group of the formula:

and wherein R' is hydrogen or a $C_{1-6}$alkyl group.

4. The compound of claim 3 wherein $P_3$ is Ile, Val or Ala.

5. The compound of claim 4 wherein $P_4$ is Ala or a bond.

6. The compound of claim 5 wherein $R_1$ is —CH(CH$_3$)$_2$.

7. The compound of claim 6 wherein $P_3$ is Val.

8. The compound of claim 7 wherein $P_4$ is a bond.

9. The compound according to claim 1 wherein the compound is N-(4-(4-morpholinyl-carbonyl)benzoyl)-L-valyl-N'-(3,3,4,4,4-pentafluoro-1-(1-methylethyl)-2-oxobutyl)-trans-4-benzyloxyprolinamide.

10. The composition comprising a compound of claim 1 and a carrier.

11. The pharmaceutical composition comprising a compound of claim 1 and a carrier.

* * * * *